(12) United States Patent
Kianl et al.

(10) Patent No.: US 6,658,276 B2
(45) Date of Patent: Dec. 2, 2003

(54) PULSE OXIMETER USER INTERFACE

(75) Inventors: Massi E. Kianl, Laguna Niguel, CA (US); Ammar Al-Ali, Tustin, CA (US); Don Carothers, Mission Viejo, CA (US); Michael Lee, Aliso Viejo, CA (US); James Pishney, Orange, CA (US); Walter M. Weber, Dana Point, CA (US)

(73) Assignee: Masimo Corporation, Irvine, CA (US)

( * ) Notice: Subject to any disclaimer, the term of this patent is extended or adjusted under 35 U.S.C. 154(b) by 11 days.

(21) Appl. No.: 10/076,860

(22) Filed: Feb. 12, 2002

(65) Prior Publication Data

US 2002/0161291 A1 Oct. 31, 2002

Related U.S. Application Data

(63) Continuation-in-part of application No. 09/641,542, filed on Aug. 18, 2000, and a continuation-in-part of application No. 09/516,110, filed on Mar. 1, 2000, now Pat. No. 6,584,336, and a continuation-in-part of application No. 09/491,175, filed on Jan. 25, 2000, now abandoned.

(60) Provisional application No. 60/268,207, filed on Feb. 12, 2001, provisional application No. 60/161,565, filed on Oct. 26, 1999, and provisional application No. 60/117,097, filed on Jan. 25, 1999.

(51) Int. Cl.$^7$ ................................................ A61B 5/00
(52) U.S. Cl. ...................................... 600/322; 600/323
(58) Field of Search ................................. 600/300, 301, 600/310, 322–324; 345/700, 864

(56) References Cited

U.S. PATENT DOCUMENTS

| | | | |
|---|---|---|---|
| 4,895,161 A | 1/1990 | Cudahy et al. | |
| 4,942,877 A | 7/1990 | Sakai et al. | |
| 5,159,936 A | 11/1992 | Yelderman et al. | |
| 5,209,343 A | 5/1993 | Romano et al. | |
| 5,332,876 A | 7/1994 | Romano et al. | |
| 5,434,964 A | 7/1995 | Moss et al. | |
| 5,473,536 A | * 12/1995 | Wimmer | 700/90 |
| 5,632,272 A | 5/1997 | Diab et al. | |
| 5,638,818 A | 6/1997 | Diab et al. | |
| 5,661,658 A | * 8/1997 | Putt et al. | 345/762 |

(List continued on next page.)

FOREIGN PATENT DOCUMENTS

| | | |
|---|---|---|
| EP | 0 601 589 | 12/1993 |
| WO | WO 97/22293 | 6/1997 |
| WO | WO 00/42911 | 7/2000 |
| WO | WO 02/15781 A1 | 2/2002 |

OTHER PUBLICATIONS

Comus International, 3 pages alleged to be downloaded and printed fromt the World Wide Web on Mar. 15, 2002.

Copending U.S. application No. 10/153,263, filed on May 21, 2002 (Atty. No. 162CP1), and pending claims.

*Primary Examiner*—Eric F. Winakur
*Assistant Examiner*—David J. McCrosky
(74) *Attorney, Agent, or Firm*—Knobbe, Martens, Olson & Bear LLP

(57) ABSTRACT

A pulse oximetry user interface has a display and a plurality of views each configured to occupy the display. Each of the views are adapted to present data responsive to a physiological signal. A plurality of icons are configured to occupy a portion of the views and adapted to designate the content of the views. Further, a plurality of keys are proximate to the display and correspond to the icons so as to select the icons. One of the views is a pleth view that presents a pulse waveform. Another one of the views is a trend view that presents a trend graph. At least one of the icons can be selected so as to switch the display between the pleth view and the trend view.

7 Claims, 30 Drawing Sheets

U.S. PATENT DOCUMENTS

| | | |
|---|---|---|
| 5,687,717 A | 11/1997 | Halpern et al. |
| 5,758,644 A | 6/1998 | Diab et al. |
| 5,782,805 A * | 7/1998 | Meinzer et al. ............. 604/151 |
| 5,860,918 A * | 1/1999 | Schradi et al. ............. 600/300 |
| 5,868,710 A | 2/1999 | Battiato et al. |
| 5,931,791 A | 8/1999 | Saltzstein et al. |
| 6,134,504 A | 10/2000 | Douglas et al. |
| 6,322,502 B1 * | 11/2001 | Schoenberg et al. ........ 600/300 |
| 6,352,504 B1 | 3/2002 | Ise et al. |
| 6,415,166 B1 * | 7/2002 | Van Hoy et al. ............ 600/323 |

* cited by examiner

— 290

— 292

— 294

— 295

— 297

— 299

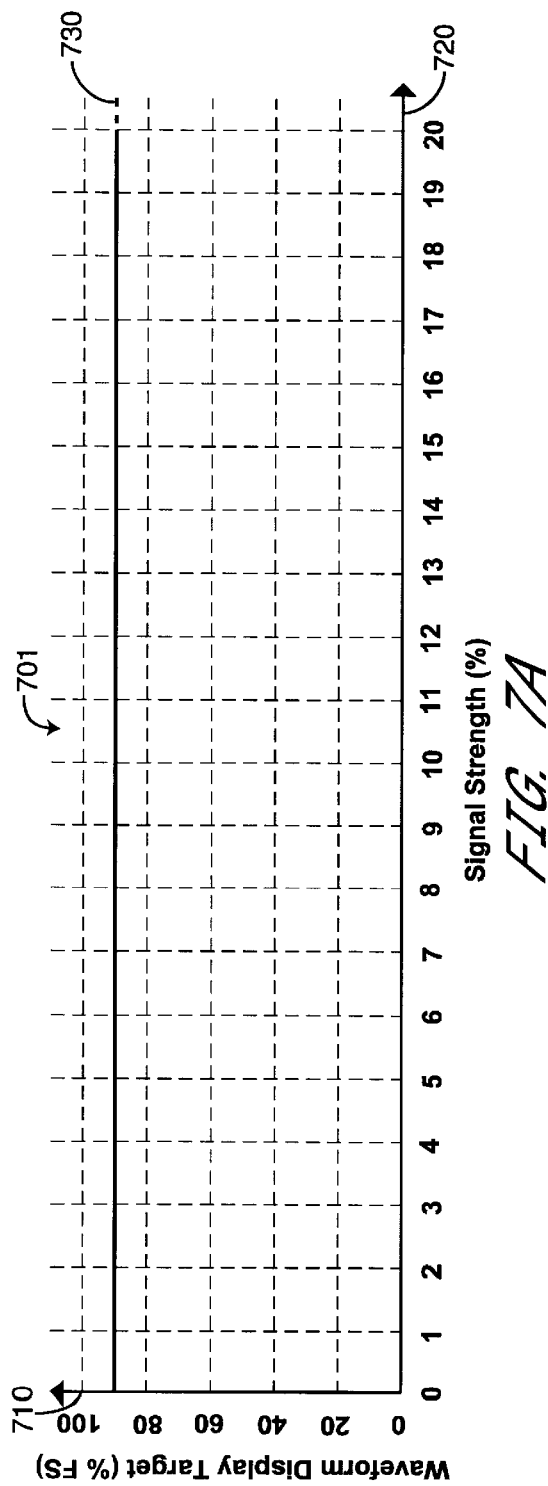
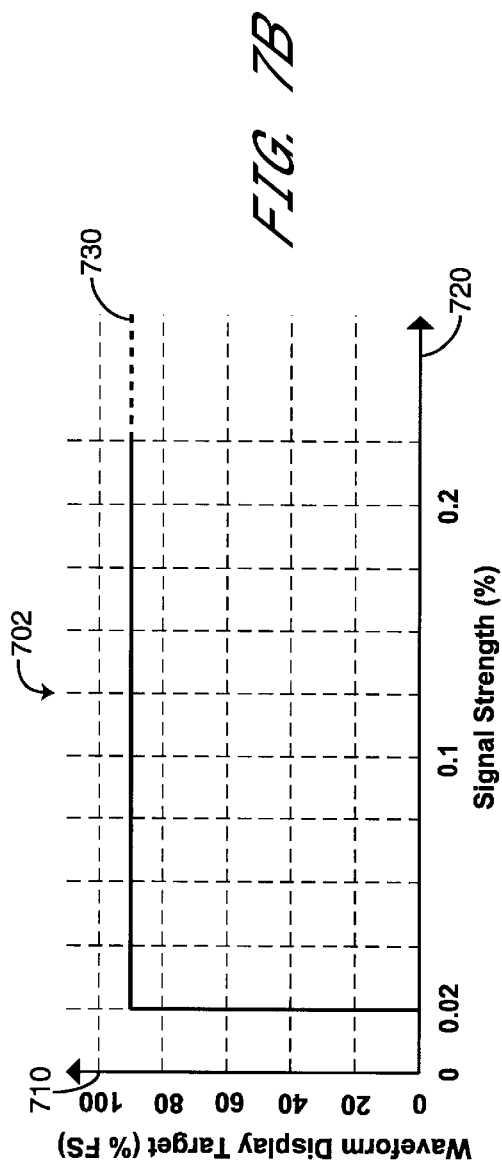
FIG. 7A
FIG. 7B

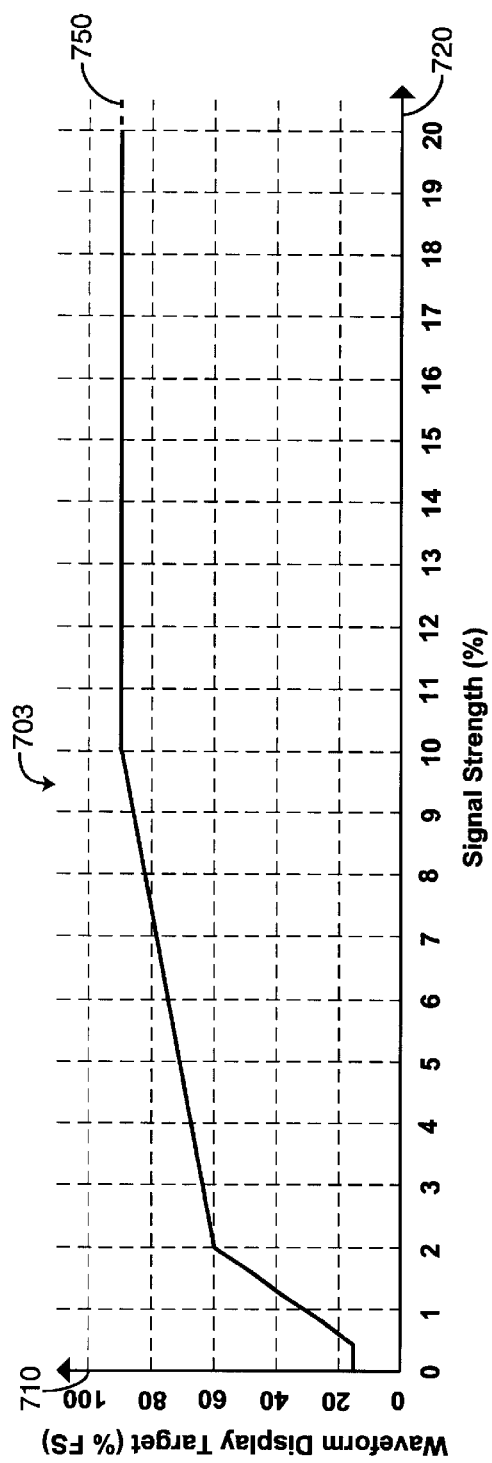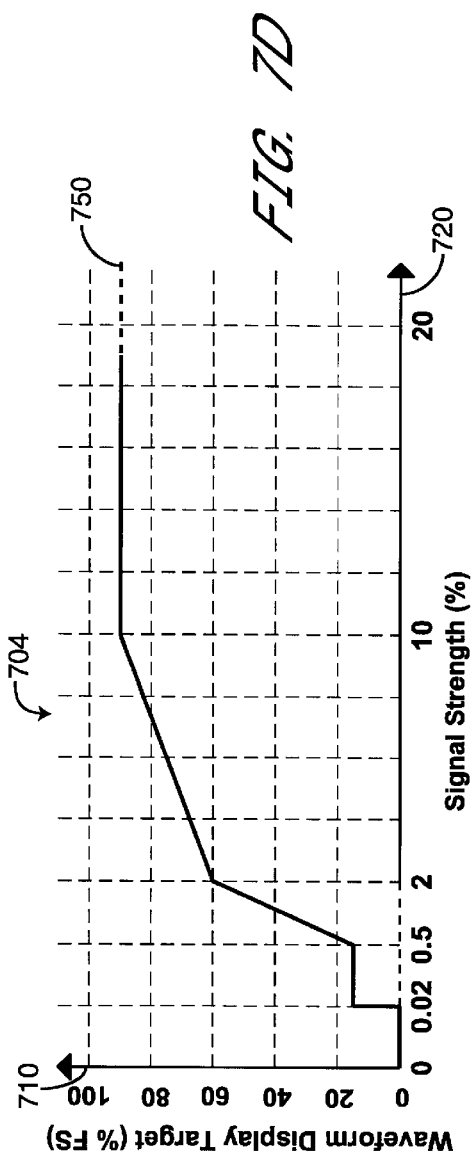

PULSE OXIMETER USER INTERFACE

CROSS-REFERENCE TO RELATED APPLICATIONS

This application claims a priority benefit under 35 U.S.C. §120 from, and is a continuation-in-part of U.S. patent application Ser. No. 09/641,542, filed Aug. 18, 2000, entitled "Dual-Mode Pulse Oximeter," No. 09/516,110, filed Mar. 1, 2000, now U.S. Pat. No. 6,584,336 entitled "Universal/Upgrading Pulse Oximeter," and No. 09/491,175, filed Jan. 25, 2000 now ABN, entitled "Universal/Upgrading Pulse Oximeter." This application also claims a priority benefit under 35 U.S.C. §119(e) from U.S. Provisional Patent Application No. 60/268,207, filed Feb. 12, 2001, entitled "Pulse Oximetry User Interface," No. 60/161,565, filed Oct. 26, 1999, entitled "Improved Universal/Upgrading Pulse Oximeter, and No. 60/117,097, filed Jan. 25, 1999, entitled "Universal/Upgrading Pulse Oximeter." Each of the foregoing applications are incorporated by reference herein. For reference, the '542 patent application is also a continuation-in-part of the '175 patent application, the '110 patent application is a continuation of the '175 patent application, and the '175 patent application claims priority to the '565 and '097 provisional patent applications.

BACKGROUND OF THE INVENTION

Pulse oximetry is a continuous and non-invasive method of measuring the level of arterial oxygen saturation in blood. The measurement is taken by placing a sensor on a patient, usually on the fingertip for adults and the hand or foot for neonates. The sensor is connected to a pulse oximetry instrument with a patient cable. The sensor collects signal data from the patient and sends it to the instrument. A pulse oximetry instrument typically displays the calculated data as a percent value for arterial oxygen saturation ($SpO_2$), as a pulse rate (PR) and as a plethysmographic waveform.

Pulse oximetry is governed by a several principles. Oxyhemoglobin (oxygenated blood) and deoxyhemoglobin (non-oxygenated blood) differ in their absorption of red and infrared light (spectrophotometry). Also, the amount of arterial blood in tissue changes with an arterial pulse (photoplethysography). Therefore, the amount of light absorbed by the varying quantities of arterial blood changes as well.

A typical pulse oximeter uses a two-wavelength pulsatile system to distinguish between oxygenated and deoxygenated blood. Signal data is obtained by passing red and infrared light through a capillary bed (for example a fingertip, a hand, a foot) and measuring changes in light absorption during the pulsatile cycle. A typical pulse oximeter utilizes a sensor with red and infrared light-emitting diodes (LEDs) that pass light through the site to a photodiode (photodetector). The photodetector receives the light, converts it into an electronic signal and sends it, via a patient cable, to the pulse oximeter for calculation.

A pulse oximeter measures and displays functional saturation, which is the amount of oxygenated hemoglobin expressed as a percentage of the hemoglobin that can transport oxygen. This is not a measure of fractional saturation, i.e. oxygenated hemoglobin expressed as a percentage of all measured hemoglobin, including measured dysfunctional hemoglobin such as carboxyhemoglobin or methemoglobin.

Oxygen saturation measurements obtained from a pulse oximeter are commonly compared to saturations calculated from the partial pressure of oxygen ($PO_2$) obtained from an arterial blood gas sample. The calculated value obtained from the blood gas sample, however, may differ from the $SpO_2$ measurement of the pulse oximeter. Different results are usually obtained from the blood gas sample if the calculated saturation is not appropriately corrected for the effects of variables that shift the relationship between $PO_2$ and saturation, such as pH, temperature, the partial pressure of carbon dioxide ($PCO_2$), and fetal hemoglobin. Also, as blood gas samples are usually taken over a period of 20 seconds (the time it takes to draw blood) a meaningful comparison can only be achieved if the core oxygen saturation of the patient is stable and not changing over the period of time that the blood gas sample is taken.

Embodiments of the present invention seeks to overcome some or al of these and other problems.

SUMMARY OF THE INVENTION

One aspect of a pulse oximetry user interface is a display and a plurality of views each configured to occupy at least a portion of the display. Each of the views are adapted to present data responsive to a physiological signal. A plurality of icons are configured to occupy a portion of the views and adapted to designate the content of the views. Further, a plurality of keys are proximate to the display and are associated with or otherwise correspond to the icons such that selection of key corresponds to selection of an icon. One of the views is a pleth view that presents a pulse waveform. Another one of the views is a trend view that presents a trend graph. At least one of the icons can be selected so as to switch the display between the pleth view and the trend view.

Another aspect of a pulse oximetry user interface is a method comprising the steps of deriving a pulse waveform responsive to a physiological signal, calculating a data trend responsive to the physiological signal and providing the pulse waveform in a first display view. Other steps include presenting at least a portion of the data trend in a second display view, selecting a first icon accessible from the first display view to switch to the second display view, and selecting a second icon accessible from the second display view to switch to the first display view.

Yet another aspect of a pulse oximetry user interface is a view means for presenting to a user data responsive to a physiological signal, a main menu means for choosing display related categories, and a category menu means for choosing display related parameters. The parameters determine the characteristic of the view means. The user interface also includes an icon means for designating the view means, accessing the menu means and altering the parameters. The interface further includes a soft key means for selecting the icon means.

For purposes of summarizing the invention, certain aspects, advantages and novel features of the invention have been described herein. Of course, it is to be understood that not necessarily all such aspects, advantages or features will be embodied in any particular embodiment of the invention.

BRIEF DESCRIPTION OF THE DRAWINGS

A general architecture that implements the various features of the invention will now be described with reference to the drawings. The drawings and the associated descriptions are provided to illustrate embodiments of the invention and not to limit the scope of the invention. Throughout the drawings, reference numbers are re-used to indicate correspondence between referenced elements. In addition, the first digit of each reference number indicates the figure in which the element first appears.

FIGS. 4–6 are illustrations of display views;

FIG. 4 illustrates a pleth only view;

FIG. 6 illustrates a numeric view;

FIGS. 7A–D are graphs of pleth auto-scaling and auto-clipping characteristics;

FIGS. 11–18 are illustrations of submenus and screens accessible from the main menu;

FIG. 12 is an illustration of a display menu;

FIG. 13 is an illustration of a general menu;

FIG. 14 is an illustration of a clock menu;

FIG. 15 is an illustration of an about screen;

FIG. 16 is an illustration of an output menu;

FIG. 17 is an illustration of a service menu;

FIG. 18 is an illustration of a password screen;

FIG. 19 is an illustration of a trend setup menu;

FIG. 20 is an illustration of a histogram screen; and

FIG. 21 is an illustration of a clear confirmation screen.

DETAILED DESCRIPTION OF THE PREFERRED EMBODIMENTS

Figure 1A:
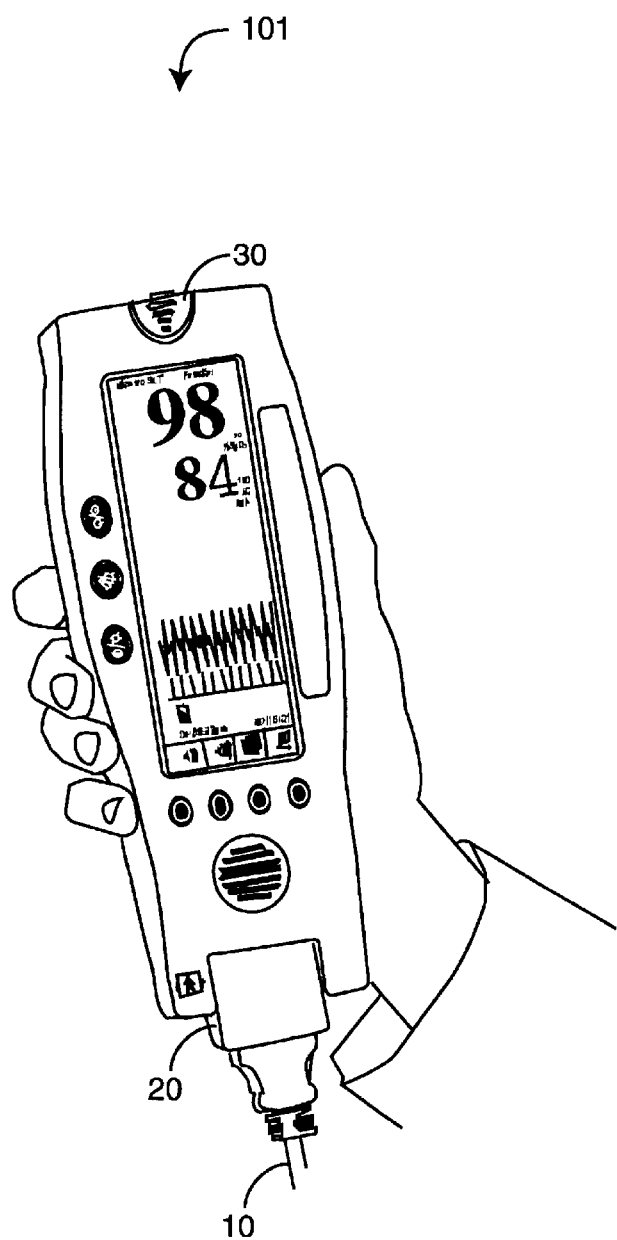
FIGS. 1A–C are perspective views of a three-in-one pulse oximeter.
Figure 1B:
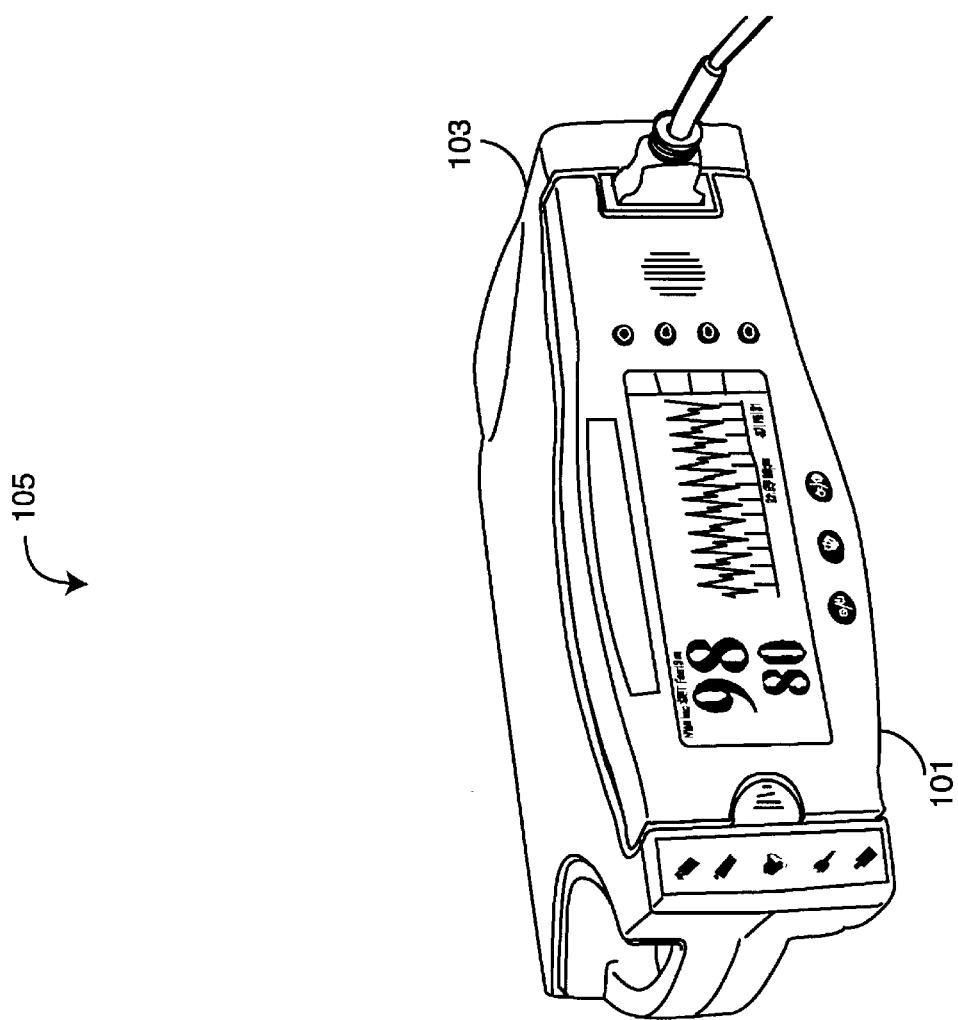
Figure 1C:
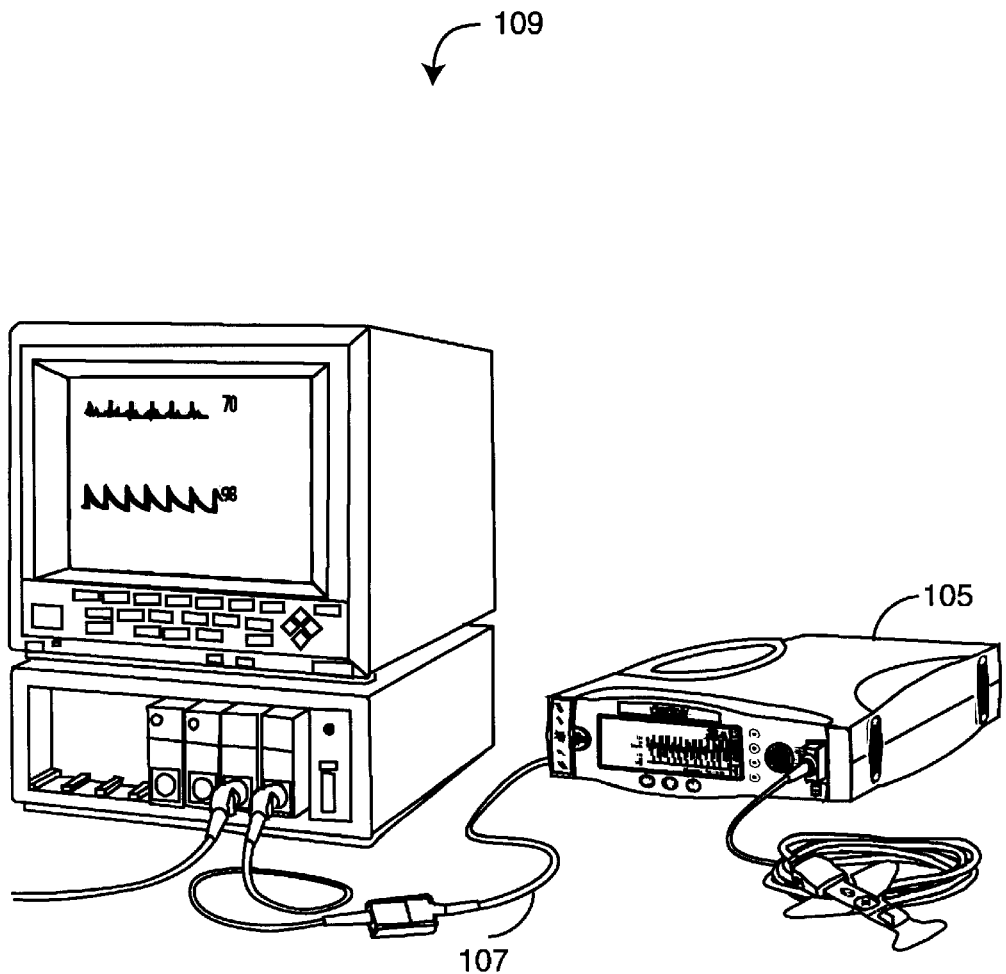

FIGS. 1A–C illustrate an instrument that provides the functionality of three pulse oximeters in one. FIG. 1A illustrates a full-featured handheld pulse oximeter 101. FIG. 1B illustrates a full-featured standalone pulse oximeter 105. FIG. 1C illustrates an upgrading pulse oximeter 109.

Figure 2A:
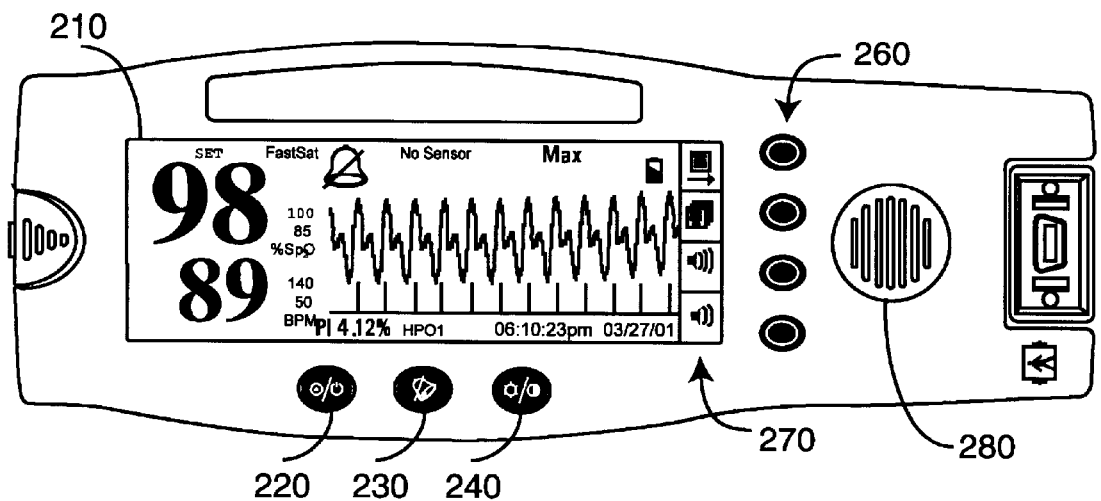
FIGS. 2A–C are illustrations of a pulse oximeter user interface.

As shown in FIG. 1A, the handheld 101 contains the majority of the pulse oximeter features. Pulse oximetry measurement information, as well as instrument status data is displayed to a user on a handheld LCD screen 210 (FIG. 2A). User input is handled through control keys 220–260 (FIG. 2A) on a front panel. User input and displays are controlled by the handheld 101. A sensor cable 10 connects into a swivel connector 20 on the handheld 100. The handheld 101 is battery powered and can be used either as a transport monitor or as a handheld pulse oximeter for spot checks. A handheld release button 30 is pressed to pull the handheld 101 out of a docking station 103 (FIG. 1B).

As shown in FIG. 1B, the handheld 101 snaps into the docking station 103 to provide the standalone pulse oximeter 105. The docking station 103 connects to AC power for standalone operation or handheld battery charging. In one embodiment, a docking station battery is also available. The standalone pulse oximeter 105 features an analog output/nurse call and a serial output that interfaces to, for example, a printer or computer.

As shown in FIG. 1C, utilizing an interface cable 107, the standalone 105 also interfaces to the sensor port of an $SpO_2$ module of a validated multiparameter patient monitor or other pulse oximeter monitor so as to upgrade conventional pulse oximetry to advanced pulse oximetry. The interface cable 107 attaches to the back of the docking station 105.

A handheld pulse oximeter, docking station, standalone pulse oximeter and interface cable are described in U.S. patent application Ser. No. 09/516,110 filed Mar. 1, 2000 entitled "Universal/Upgrading Pulse Oximeter," assigned to the assignee of the present invention and incorporated by reference herein. Pulse oximeters having handheld, docking stations and standalone features include those commercially available from, for example, Masimo Corporation of Irvine, Calif., under the Radical™ brand. An associated publication entitled "Radical, Signal Extraction Pulse Oximeter, Operator's Manual," ©2001 Masimo Corporation is incorporated by reference herein. Interface cables are also available from, for example, Masimo Corporation under the SatShare™ brand.

Handheld Pulse Oximeter

Figure 2B:
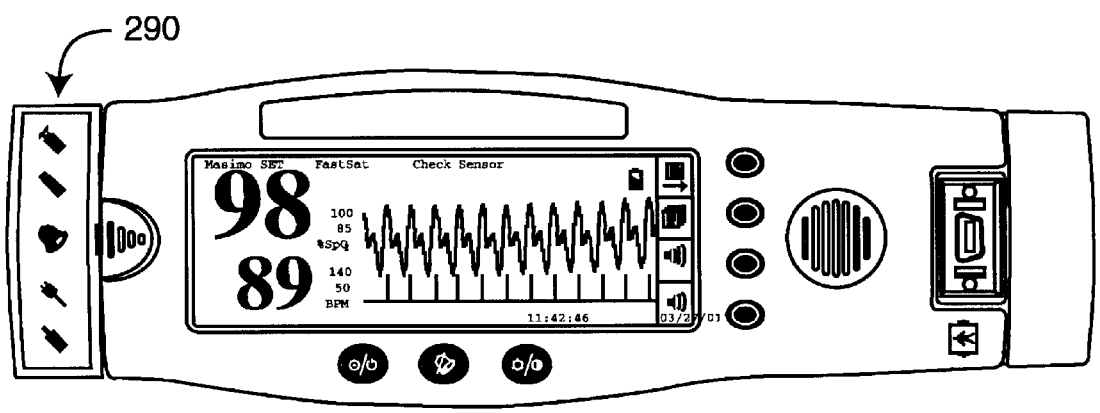
Figure 2C:
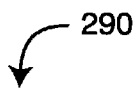
Figure 2C:
Figure 2C:
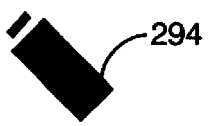
Figure 2C:
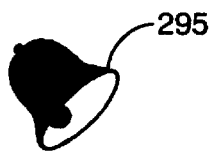
Figure 2C:
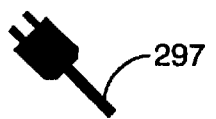
Figure 2C:

FIGS. 2A–C generally illustrate a pulse oximeter user interface. FIG. 2A illustrates a handheld user interface having the display 210, the fixed function keys 220–240, programmable function keys ("soft keys") 260, associated soft key icons 270 and a loudspeaker 280. The loudspeaker 280 provides an audio indication of alarms, which are described with respect to FIGS. 11A–B, below. The display 210 is described with respect to FIGS. 4–6, below. The four soft keys 260 are pressed to select a corresponding one of the soft key icons 270. The soft key icons 270 indicate the software menu items that can be selected through the soft keys 260. Pressing a soft key 260 next to an icon 270 selects the option. The soft keys 260 and soft key icons 270 are described with respect to FIGS. 8A–B, below.

As shown in FIG. 2A, the fixed function keys 220–240 include a power/standby button 220, an alarm silence button 230 and a backlight/contrast button 240. The power/standby button 220 is pressed to turn the instrument on, and it is held down for more than 2 seconds and then released to turn the instrument off.

The alarm silence button 230 is pressed to temporarily silence patient alarms. Also, the alarm silence button 230 is pressed when SENSOR OFF or NO SENSOR messages are flashing, such as when the sensor is removed from the patient, to acknowledge the end of monitoring. In these states, all further alarms are suspended until the pulse oximeter starts measuring oxygen saturation (i.e. $SpO_2$) and pulse rate again. System fault alarms can be silenced by pressing the power/standby button 220 or the alarm silence button 230.

The backlight/contrast button 240 is pressed to change the illumination level of the backlight. With the AC line power connected, four levels of illumination are available in addition to a no illumination level. In the handheld mode, three levels of illumination are available in addition to a no illumination level. The lowest illumination is used for the most efficient battery usage. The backlight/contrast button 240 is also used to change the contrast of the LCD display by pressing and holding it for longer than two seconds to begin the contrast change and releasing it at the desired contrast setting.

Standalone Pulse Oximeter

FIG. 2B illustrates a standalone user interface having LED indicators 290 in addition to some or all of the interface features of the handheld, described above. When the handheld is placed into the docking station, the handheld can become a full-featured standalone pulse oximeter. The standalone acts as a battery charger for the handheld and has AC power connection capabilities. The standalone can also interface to serial devices, nurse call or analog output devices, and multiparameter patient monitors through an interface cable.

FIG. 2C illustrates the standalone LED indicators 290 including a docking station battery charging indicator 292, a handheld battery charging indicator 294, a visual alarm indicator 295, an AC power indicator 297 and a docking indicator 299. The docking station battery charging indicator 292 is illuminated when the docking station battery is charging. The handheld battery charging indicator 294 also is illuminated when the handheld battery is charging. Both charging indicators 292, 294 blink just prior to charging. Neither charging indicator 294 illuminates when a battery is fully charged or when a battery is not present. The visual alarm indicator 295 is illuminated when an alarm condition is active and the alarm status indicator is shown. The AC power indicator 297 is illuminated when the docking station is plugged into AC line power. The docking indicator 299 is illuminated when the handheld is turned on and is properly interfaced to a docking station. When the standalone is turned on at start up, all indicator LEDs initially turn on and off.

User Interface Details

Figure 3:
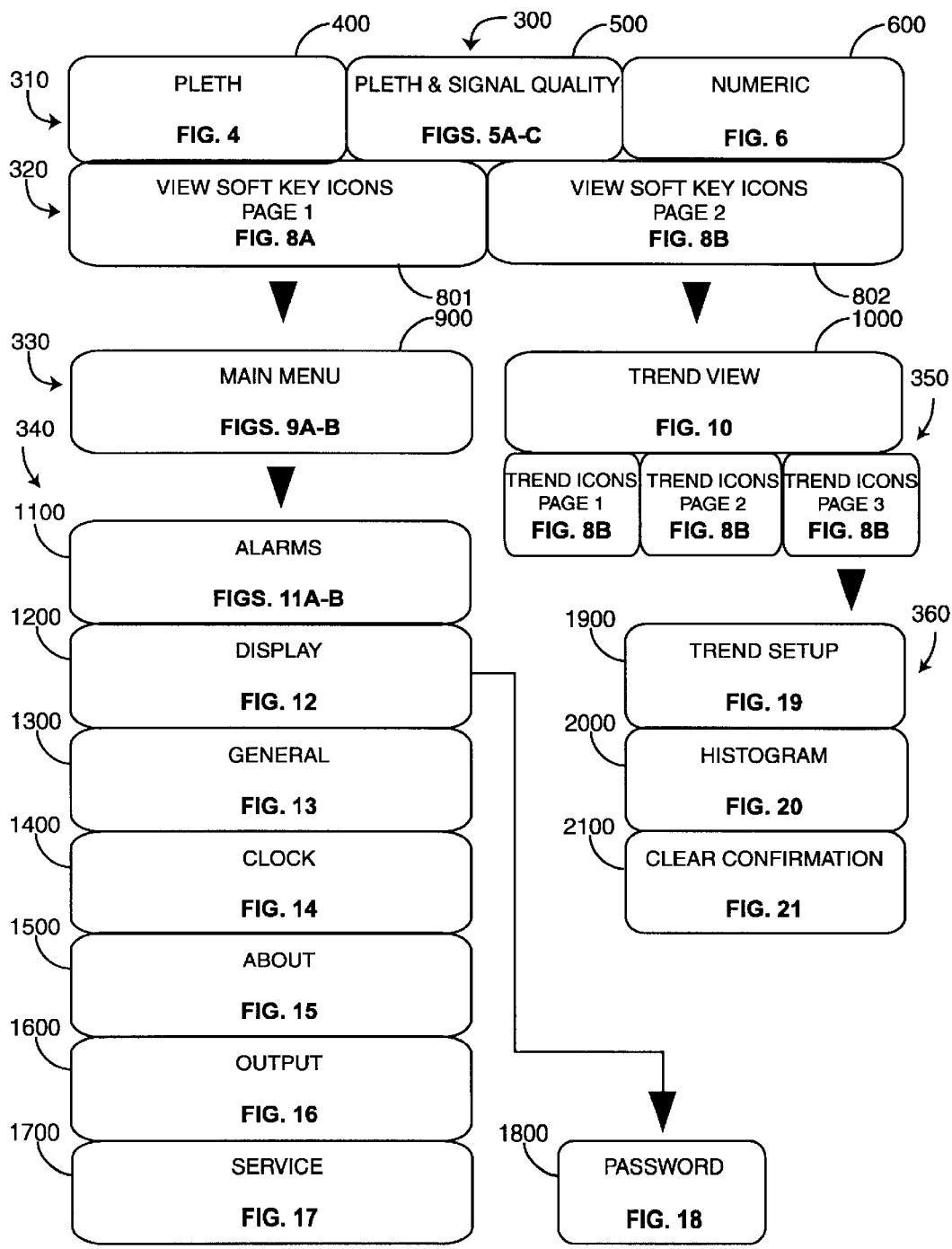
FIG. 3 is a hierarchical chart of a pulse oximeter user interface.

FIG. 3 provides a hierarchical overview 300 of the content of the user display 210 (FIG. 2A) having display views 310, display view soft key icons 320, main menu and trend view 330, submenus 340, trend soft key icons 350 and trend-related screens 360. There are three display views 310 including a pleth only view 400, described with respect to FIG. 4, a pleth and signal quality view 500, described with respect to FIGS. 5A–C, and a numeric view, described with respect to FIG. 6.

As shown in FIG. 3, there are two pages of soft key icons 320 that appear in the display views 310. A first page of icons 801 includes a main menu icon 814 (FIG. 8A) that, when selected, provides a main menu 900. The main menu 900 includes soft key icons 820 (FIG. 8A) that allow selection of the submenus 340. A second page of icons 802 include a trend icon 864 (FIG. 8B) that, when selected, provides a trend view 1000. The trend view 1000 includes three pages of trend soft key icons 350. One of the trend soft key icon pages 350 provides for the selection of the trend-related screens 360. The display view icons 320, main menu icons 820 (FIG. 8A), and trend icons 350 are described with respect to FIGS. 8A–B, below. The main menu 900 is described with respect to FIGS. 9A–B, below, and the trend view 1000 is described with respect to FIG. 10, below. The submenus 340 are described with respect to FIGS. 11–17, below. The general submenu 1300 provides for the selection of a home mode and associated password screen 1800, described with respect to FIG. 13 and FIG. 18, below.

The content of the user display 210 (FIG. 2A) can appear as a horizontal format or a vertical format. The content of the user display 210 (FIG. 2A) can rotate between display formats as the handheld 101 (FIG. 1A) or standalone 105 (FIG. 1B) are physically moved to corresponding horizontal or vertical positions. Alternatively, the display content can rotate between horizontal and vertical formats by selection of a rotate soft key icon 868 (FIG. 8B), described below. Horizontal and vertical format pairs are illustrated in FIGS. 5A–B, 9A–B, and 11A–B. A rotatable format display is described in U.S. patent application Ser. No. 09/516,110, referenced above.

Display Views

Pleth View

Figure 4:
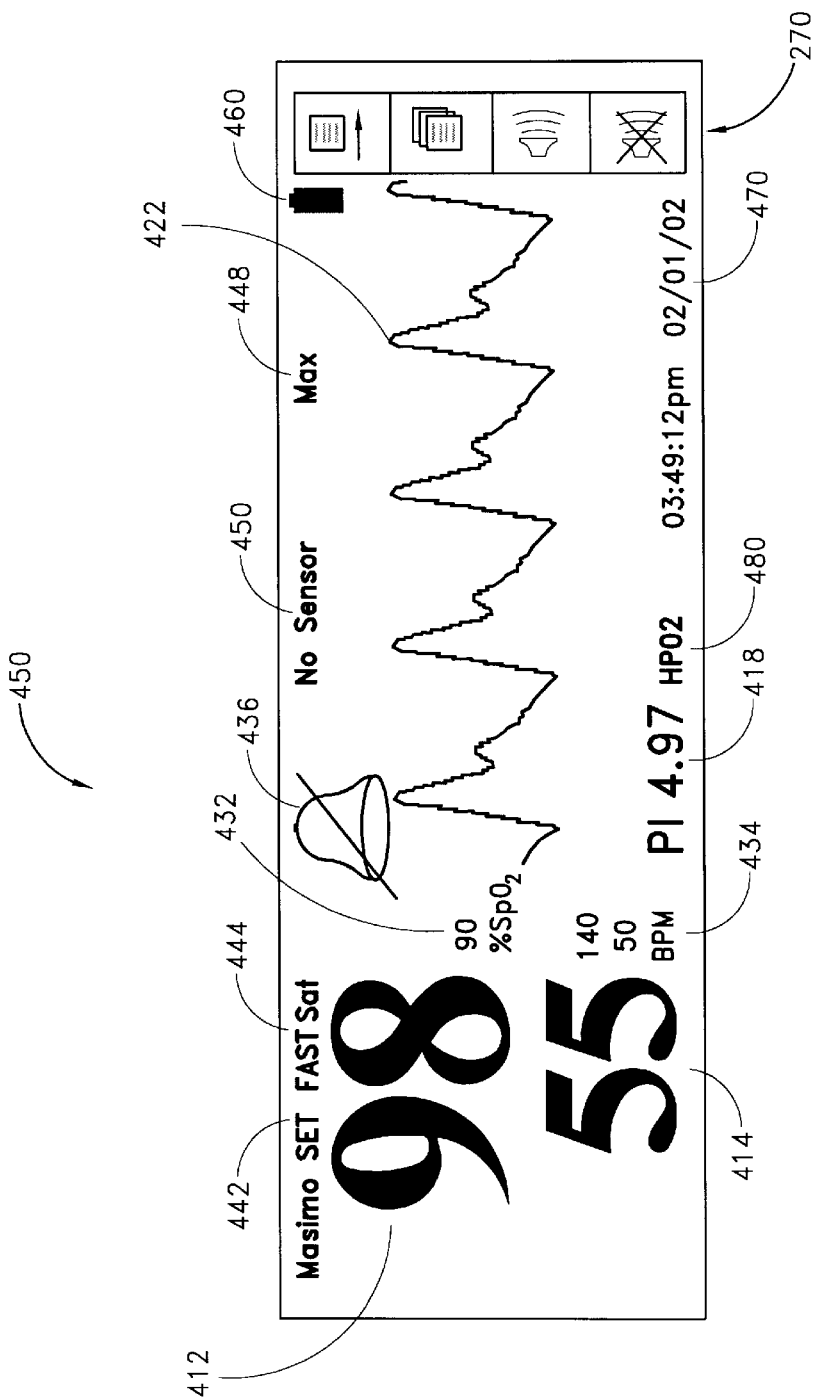

FIG. 4 illustrates a pleth only view 400 having an oxygen saturation 412, a pulse rate 414, a perfusion index 418 and a pulse waveform 422. The oxygen saturation 412 displays a functional arterial hemoglobin oxygen saturation measurement in units of percentage $SpO_2$. When a sensor is not connected to a patient and during pulse search, the display will show dashed lines. The oxygen saturation 412 is calculated and the display is updated at a frequency of once per second. The pulse rate 414 displays a patient's pulse rate in beats per minute. The pulse rate 414 is calculated and the display is updated at a frequency of once per second.

The pulse waveform 422 displays the acquired plethysmograph ("pleth"). The pulse waveform 422 is scaled with signal strength, as described in detail with respect to FIGS. 7A–D, below. The pulse waveform 422 is updated at a frequency of 31.25 times per second. The perfusion index 418 displays the percentage of pulsatile signal to non-pulsatile signal.

As shown in FIG. 4, the pleth view 400 also has saturation limits 432, pulse rate limits 434 and an alarm status indicator 436. The saturation limits 432 display the upper and lower saturation alarm limits. The saturation limits 432 are displayed next to the oxygen saturation 412. The pulse rate limits 434 display the upper and lower pulse rate alarm limits. The pulse rate limits 434 are displayed next to the pulse rate 414. When a measured value reaches or exceeds an alarm limit 432, 434 the associated number display 412, 414 and the corresponding violated limit 432, 434 flash.

The alarm status indicator 436 is a bell symbol that can be shown with or without a slash. It flashes when an alarm condition is present. When the alarm is silenced using the alarm silence button 230 (FIG. 2A), an alarm status indicator 436 with a slash and a timer is shown to indicate that the alarm is temporarily silenced. When the alarm is silenced through an "all mute" menu selection, which is permanent until power is cycled or deselected using menu, an alarm status indicator 436 with a slash is shown to indicate that alarm has been silenced.

Also shown in FIG. 4, the pleth view 400 has status messages 442–448 and indicators 460–480. The status messages include an advanced signal processing message ("Masimo SET") 442 when such processing is active, a fast signal processing message ("FastSat") 444 when operating in that mode, and a maximum sensitivity message ("Max") 448 when operating in that mode. The advance signal processing can include advanced pulse oximetry such as that commercially available from Masimo Corporation of Irvine, Calif. under the Masimo SET® brand. Fast signal processing is described in U.S. patent application Ser. No. 09/586,845 entitled "Variable Mode Averager," assigned to the assignee of the present invention and incorporated by reference herein.

Figure 14:
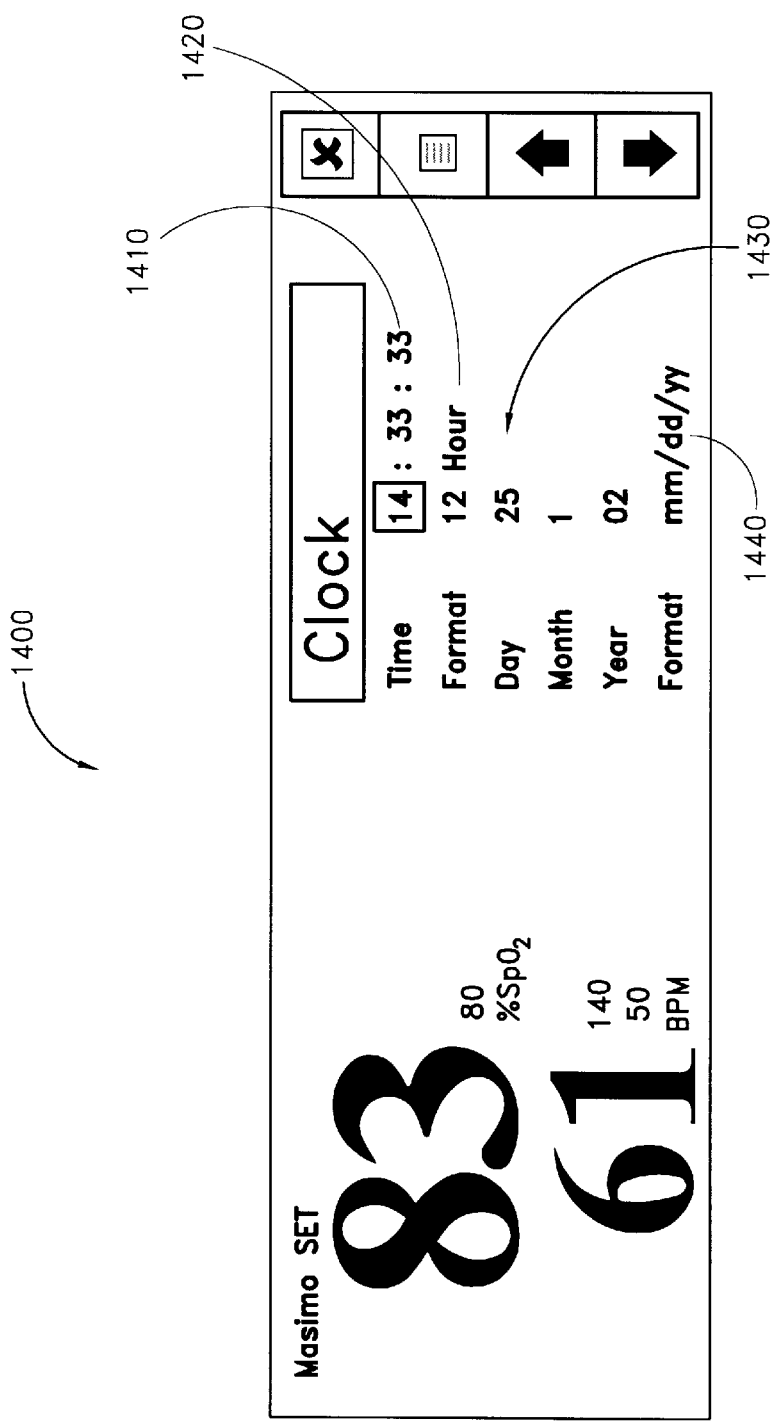

The indicators include battery status indicators 460, time and date indicators 470 and an output mode indicator 480. Battery status indicators 460 show the capacity of the handheld and optional docking station batteries. An indicator 460 flashes when less than 15 minutes of battery life is left and the battery needs to be recharged. The docking station battery status indicator is not shown when the optional docking station battery is not present. The time and date indicators 470 display the current time and date. The date and time are displayed in dd/mm/yyyy or mm/dd/yyyy format. The date and time display format is selected in the clock menu 1400 (FIG. 14). The output mode indicator 480 displays the output mode selected by the user. The output mode indicator 480 also displays the type of interface cable. In are embodiment, the output mode indicator 480 is only displayed when the instrument actively outputs data other than ASCII text or interfaces with a monitor through the interface cable.

Further shown in FIG. 4, the pleth view 400 has system messages generated by the instrument that are displayed in a system message area 450. Each message and its meaning are described immediately below. An "AMBIENT LIGHT" message indicates that too much light is on the patient (sensor). A "DEFECTIVE SENSOR" message indicates that the oximeter cannot identify the connected sensor or the sensor has failed, which, for example, may be caused by a broken sensor cable wire, inoperative LEDs, an unauthorized sensor, or a faulty detector. An "INTERFERENCE" message indicates that an outside signal or energy is preventing a reading. An "INVALID SENSOR" message indicates the oximeter cannot identify the connected sensor, which again can be due to a broken sensor cable wire, inoperative LEDs, an unauthorized sensor, or a faulty detector. A "LOW BATTERY" message indicates that the battery charge is low, signaling that the handheld be placed into the docking station to be powered with AC line power or that the battery be replaced. A "LOW PERFUSION" message indicates that the signal is too small. A "LOW SIGNAL IQ" message indicates a low signal quality, and is discussed further with respect to FIGS. 5A–C, below. A "NO SENSOR" message indicates that a sensor is not fully inserted into the connector, which may be due to an incorrect sensor, or a defective sensor or cable, or that the sensor is inserted upside down. A "PULSE SEARCH" message indicates that the instrument is searching for patient's pulse. A "SENSOR OFF" message indicates that a sensor is off the patient and should be reattached. A "SERVICE REQUIRED" message indicates an internal failure and that the instrument requires service. The "SERVICE REQUIRED" message fills the entire display.

As shown in FIG. 4, the pleth view 400 has soft key icons 270 as described with respect to FIG. 2A, above. In the display views 400–600 (FIG. 3), including the pleth view 400, the soft key icons 270 can be page 1 display view icons 810 (FIG. 8A) or page 2 display view icons 860 (FIG. 8B), described below.

Pleth And Signal Quality View

Figure 5A:
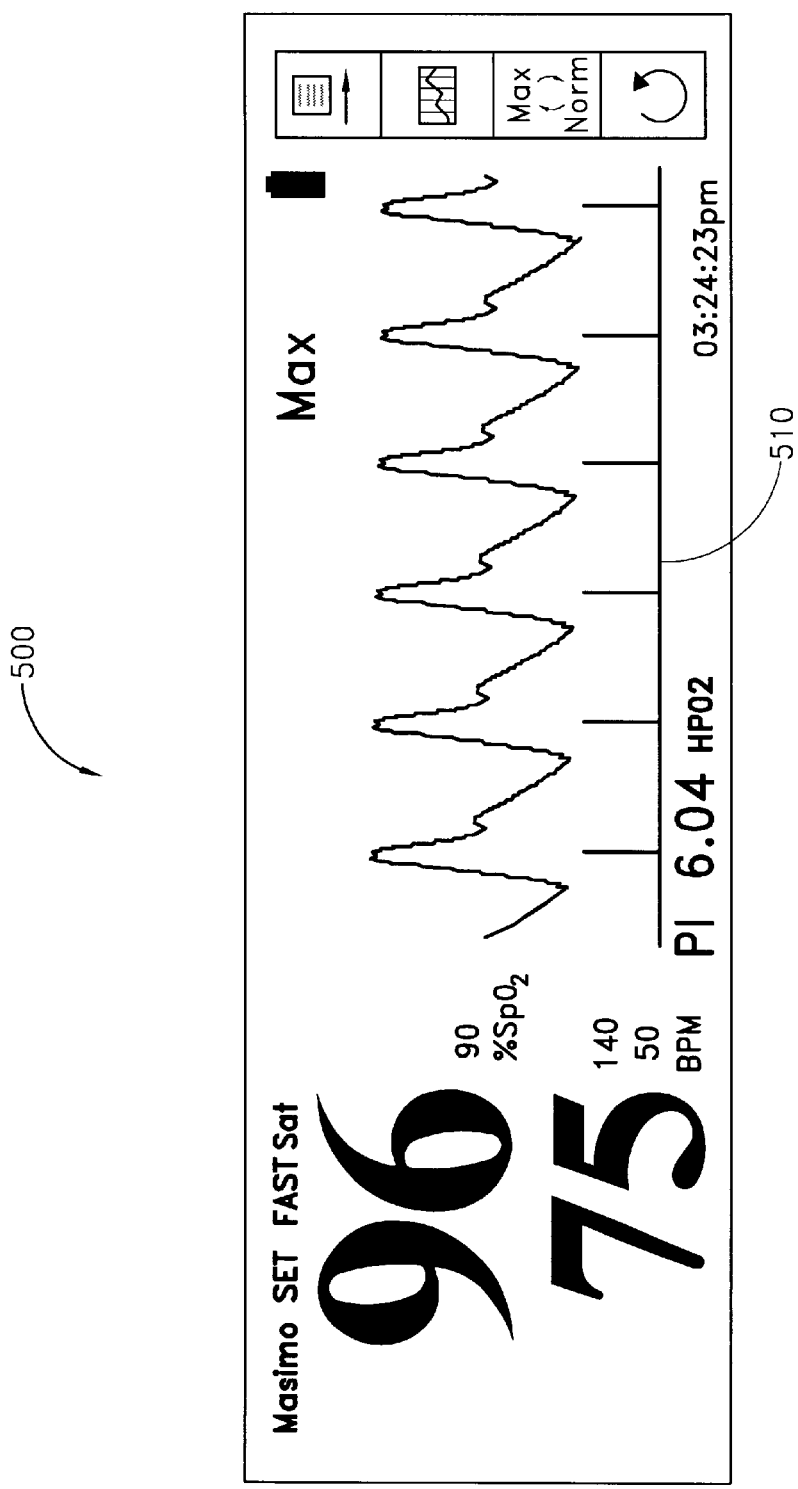
FIGS. 5A–B illustrate horizontal and vertical formats, respectively, of a pleth and signal quality view.
Figure 5B:
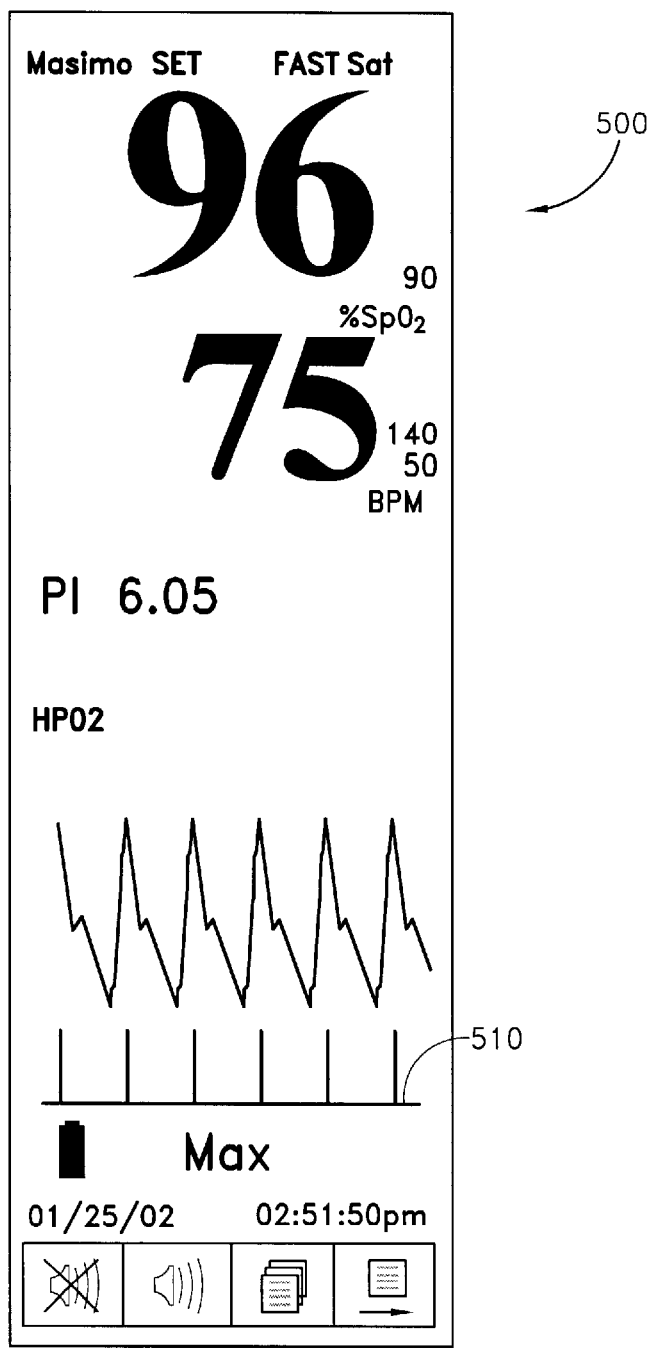

FIGS. 5A–B illustrate a pleth and signal quality view 500, in horizontal and vertical format, respectively, having the features of the pleth only view 400 (FIG. 4) in addition to a signal quality waveform 510. The signal quality waveform 510 provides a visual indicator of the plethysmogram signal quality. In particular, the signal quality waveform 510 displays the acquired signal quality and the timing of a patient's pulse by a series of vertical lines 512. With motion, the plethysmographic waveform is often distorted and may be obscured by one or more artifacts. The vertical lines 512 coincide with peaks of an arterial pulsation. Even with a plethysmographic waveform obscured by artifacts, the instrument locates the arterial pulsation. A pulse tone generated by the loudspeaker 280 (FIG. 2), when enabled, coincides with the vertical lines 512. The height of a particular vertical line of the signal quality waveform 510 indicates the quality of the measured signal. A generally large vertical line indicates that the $SpO_2$ measurement is based on a good quality signal. A generally small vertical line indicates that the $SpO_2$ measurement is based on data with low signal quality. When the signal quality is very low the accuracy of the $SpO_2$ measurement may be compromised and the "LOW SIGNAL IQ" system message 450 (FIG. 4) is displayed, as described above. The signal quality waveform 510 is updated at a frequency of 31.25 times per second. Signal quality may also be shown as a single, pulsating bar 610 (FIG. 6), as described with respect to the numeric view 600 (FIG. 6), below. Signal quality is described in U.S. patent application Ser. No. 09/858,114 entitled "Pulse Oximetry Data Confidence Indicator," assigned to the assignee of the present invention and incorporated by reference herein.

Low signal quality may be due to various factors, such as improper sensor application, misalignment of the sensor's emitter and detector resulting in smaller signals, extreme changes in the patient's physiology and blood flow at the monitoring site, such as an inflated blood pressure cuff, a squeezing motion, sampling of an arterial blood specimen from the hand containing the pulse oximetry sensor, severe hypotension, peripheral vasoconstriction in response to hypothermia, medications, or a spell of Raynaud's syndrome. With neonates or infants, the peripheral blood flow to the sensor site may occur as the result of lifting or crossing of their legs, such as during a diaper change.

Numeric View

Figure 6:
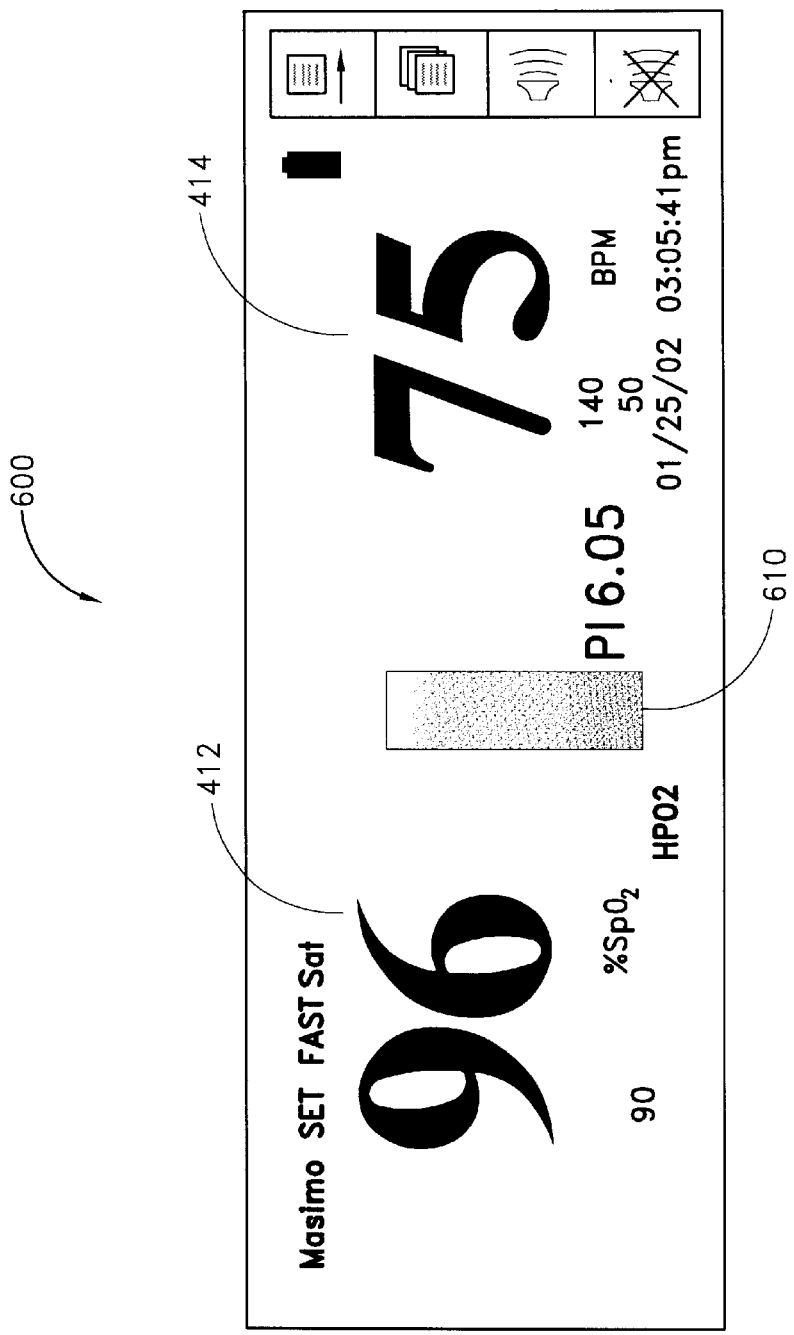

FIG. 6 illustrates a numeric view 600 having the features of the pleth view 400 (FIG. 4) without the pulse waveform 422 (FIG. 4). In particular, the numeric view prominently displays oxygen saturation 412 and pulse rate 414. Further, the numeric view 600 features a signal quality bar 610 having a pulsating height that is responsive to the patient's arterial pulse and to signal quality. Signal quality is described with respect to FIGS. 5A–B, above. Specifically, the bar height pulses coincide with peaks of an arterial pulsation and the bar height indicates signal quality, with a generally small bar height corresponding to low signal quality and a generally large bar height corresponding to high signal quality.

Stability of the oxygen saturation 412 readings may be a good indicator of signal validity. Although stability is a relative term, experience provides a good feeling for changes that are artifactual or physiological and the speed, timing, and behavior of each. The stability of the oxygen saturation 412 readings over time is affected by the averaging mode being used. The longer the averaging time, the more stable the readings tend to become. This is due to a dampened response as the signal is averaged over a longer period of time than during shorter averaging times. However, longer averaging times delay the response of the oximeter and reduce the measured variations of $SpO_2$ and pulse rate (PR). Inaccurate measurements may be caused by significant levels of dysfunctional hemoglobin (e.g., carboxyhemoglobin or methemoglobin), intravascular dyes such as indocyanine green or methylene blue, venous pulsations at the frequency of the patient's arterial pulse and very low hemoglobin levels.

The displayed pulse rate 414 may differ slightly from the heart rate displayed on ECG monitors due to differences in averaging times. There may also be a discrepancy between cardiac electrical activity and peripheral arterial pulsation. Significant differences may indicate a problem with the signal quality due to physiological changes in the patient or one of the instruments or application of the sensor or patient cable. The pulsations from intra-aortic balloon support can be additive to the pulse rate displayed on the pulse oximeter.

Pleth Auto-Scaling And Auto-Clipping

FIGS. 7A–D illustrate auto-scaling and auto-clipping characteristics for the pulse waveform 422 (FIG. 4) available on the pleth view 400 (FIG. 4) or pleth and signal quality view 500 (FIGS. 5A–C). The measured signal strength can vary quite widely. However, in a preferred embodiment, the signal strength can vary from 0% to 100%. In a more preferred embodiment, the signal strength can vary from 02% to 20%. The challenge is to display a measured waveform having three orders of magnitude dynamic range in a meaningful way. FIG. 7A illustrates an auto-scale/auto-clip graph 701 having a display target axis 710 in units of percentage of full-scale and a signal strength axis 720 in units of percentage of DC. Plotted on the graph 701 is a scaling/clipping curve 730, which illustrates the display characteristics for the pulse waveform 422 (FIG. 4) at various measured signal levels. FIG. 7B illustrates an expanded graph 702 corresponding to FIG. 7A for values along the signal strength axis 720 in a range from about 0 to 0.2%. FIGS. 7A–B illustrate one auto-scaling and auto-clipping embodiment, where the measured pulse waveform is scaled to about a 90% full-scale value for all signal strength values above about 0.02% and clipped to about 0 for all signal strength values below about 0.02%.

FIG. 7C illustrates an auto-scale/auto-clip graph 703 similar to 701 (FIG. 7A). Plotted on the graph 703 is a scaling/clipping curve 750, which illustrates the display characteristics for the pulse waveform 422 (FIG. 4) at various measured signal levels. FIG. 7D illustrates an expanded graph 704 corresponding to FIG. 7C for values along the signal strength axis 720 in a range from about 0 to 0.5%. FIGS. 7C–D illustrate another auto-scaling and auto-clipping embodiment where the measured pulse waveform is scaled to between about 15% and 90% full-scale in a piecewise linear fashion for signal strength values above about 0.02% and clipped to about 0 for all signal strength values below about 0.02%. In this manner, the displayed pulse waveform 422 (FIG. 4) advantageously conveys to the user meaningful information about the measured signal strength. Specifically, for signal strength in the range of about 10%–20%, the pulse waveform 422 (FIG. 4) is scaled to about 90% full-scale. For signal strength in the range of about 2% to 10%, the pulse waveform 422 (FIG. 4) is scaled linearly to a corresponding range of about 60% to 90% full-scale. For signal strength in the range of about 0.5% to 2%, the pulse waveform 422 (FIG. 4) is scaled linearly to a corresponding range of about 15% to 60% full-scale. For signal strength in the range of about 0.02% to 0.5%, the pulse waveform 422 (FIG. 4) is scaled to about 15% full-scale. For signal strength in the range of about 0 to 0.02%, the pulse waveform 422 (FIG. 4) is clipped to about 0.

Soft Keys

Figure 8A:
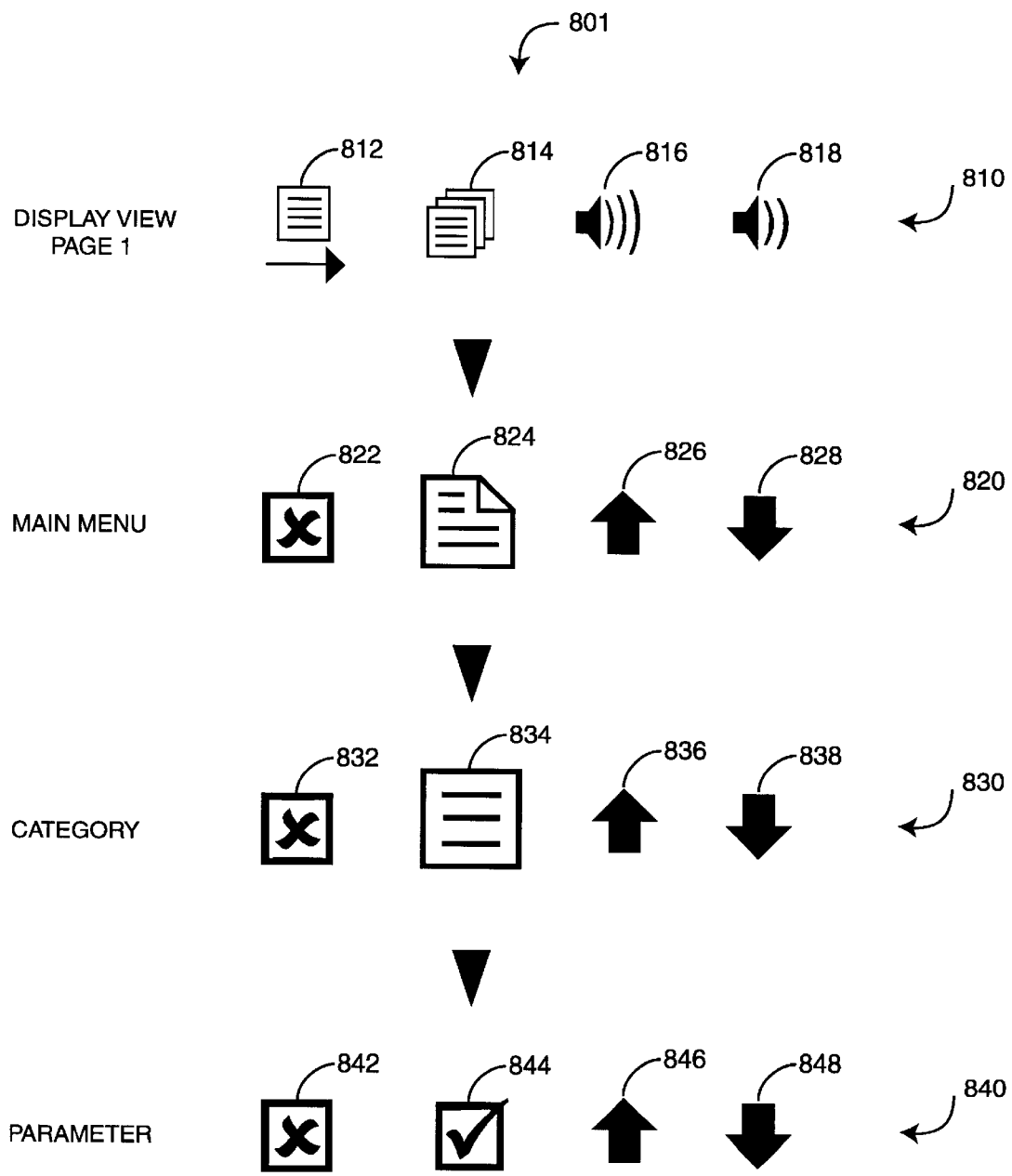
FIGS. 8A–B are hierarchical charts of soft key icons.
Figure 8B:
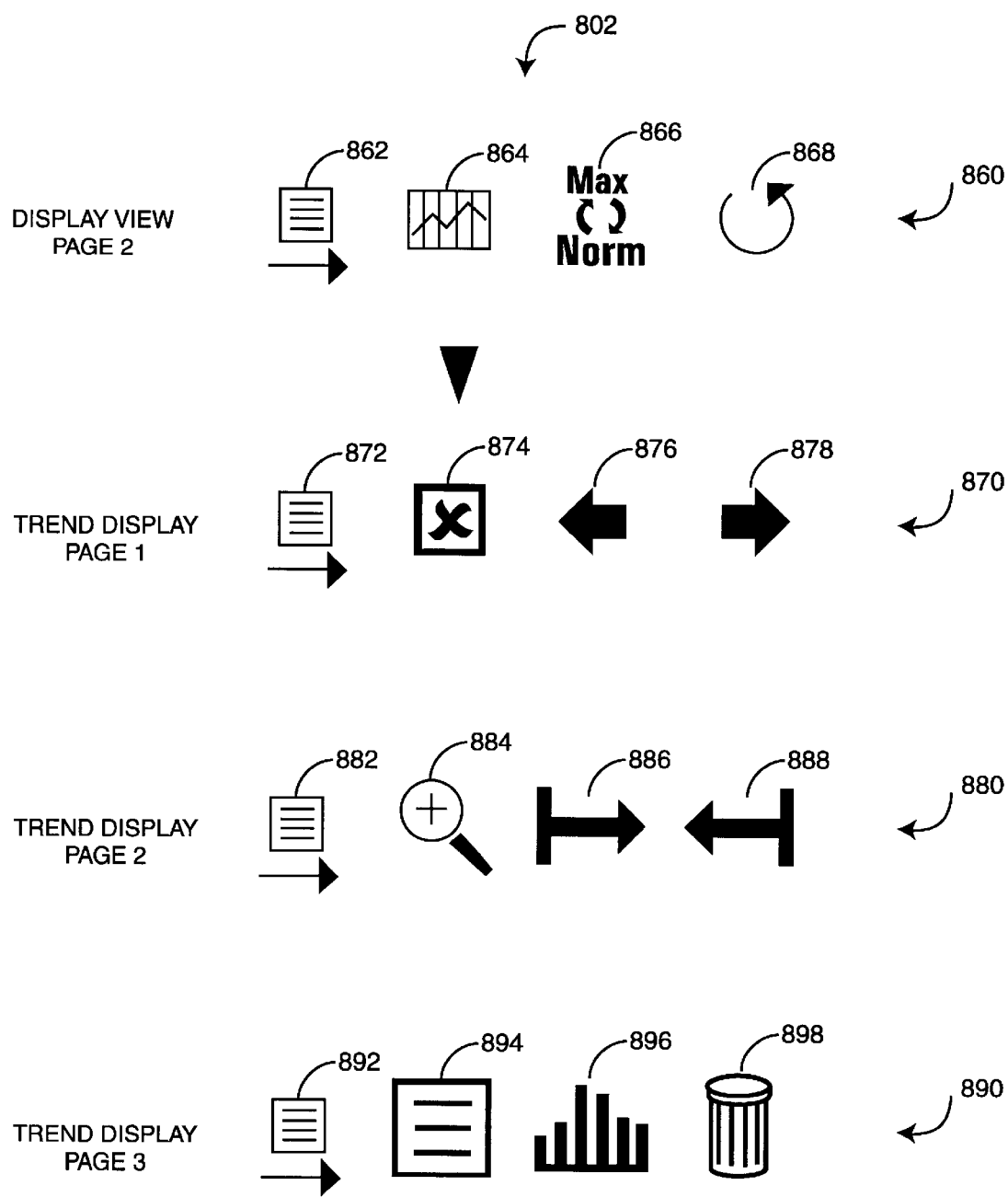
Figure 9A:
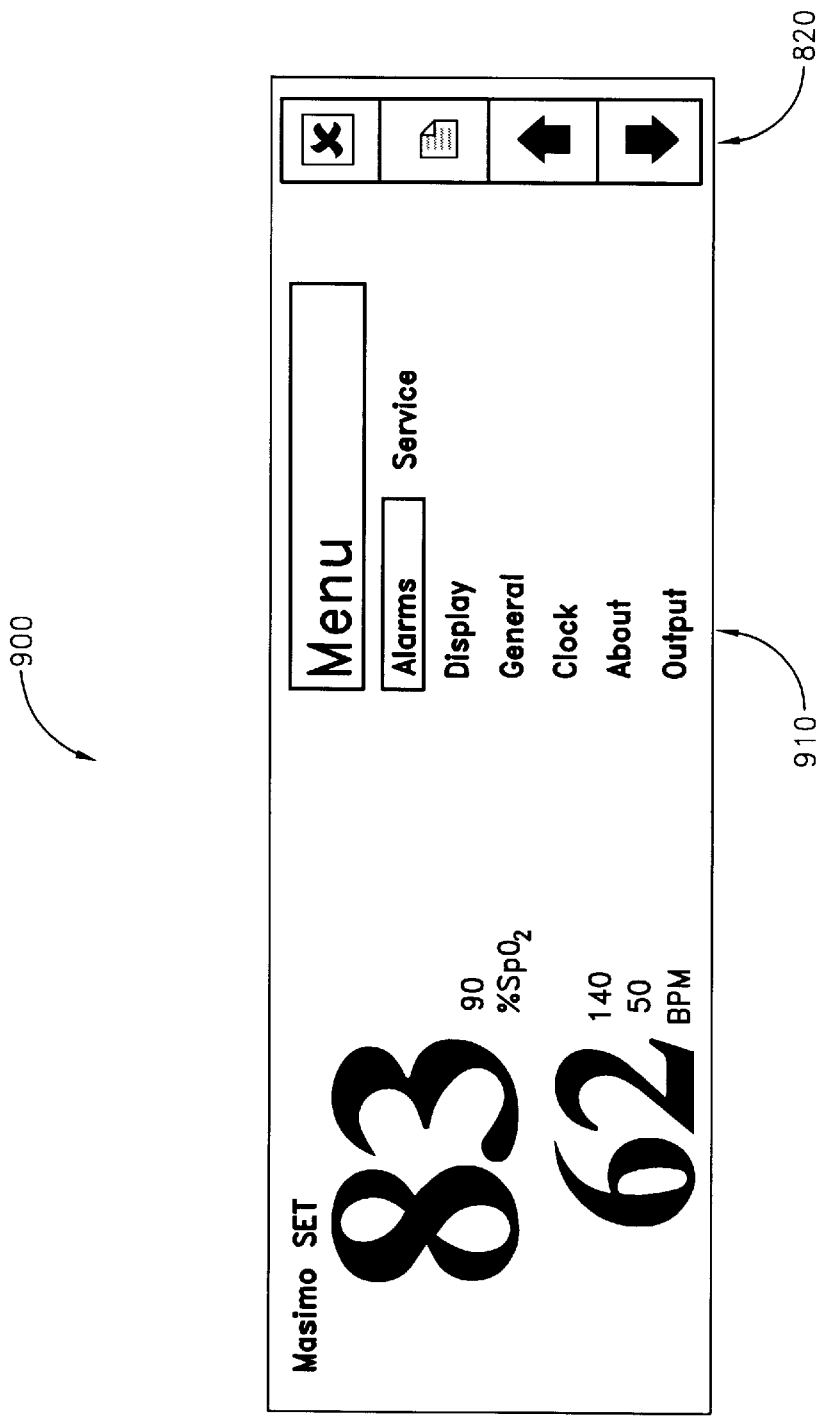
FIGS. 9A–B illustrate horizontal and vertical formats, respectively, of a main menu.
Figure 9B:
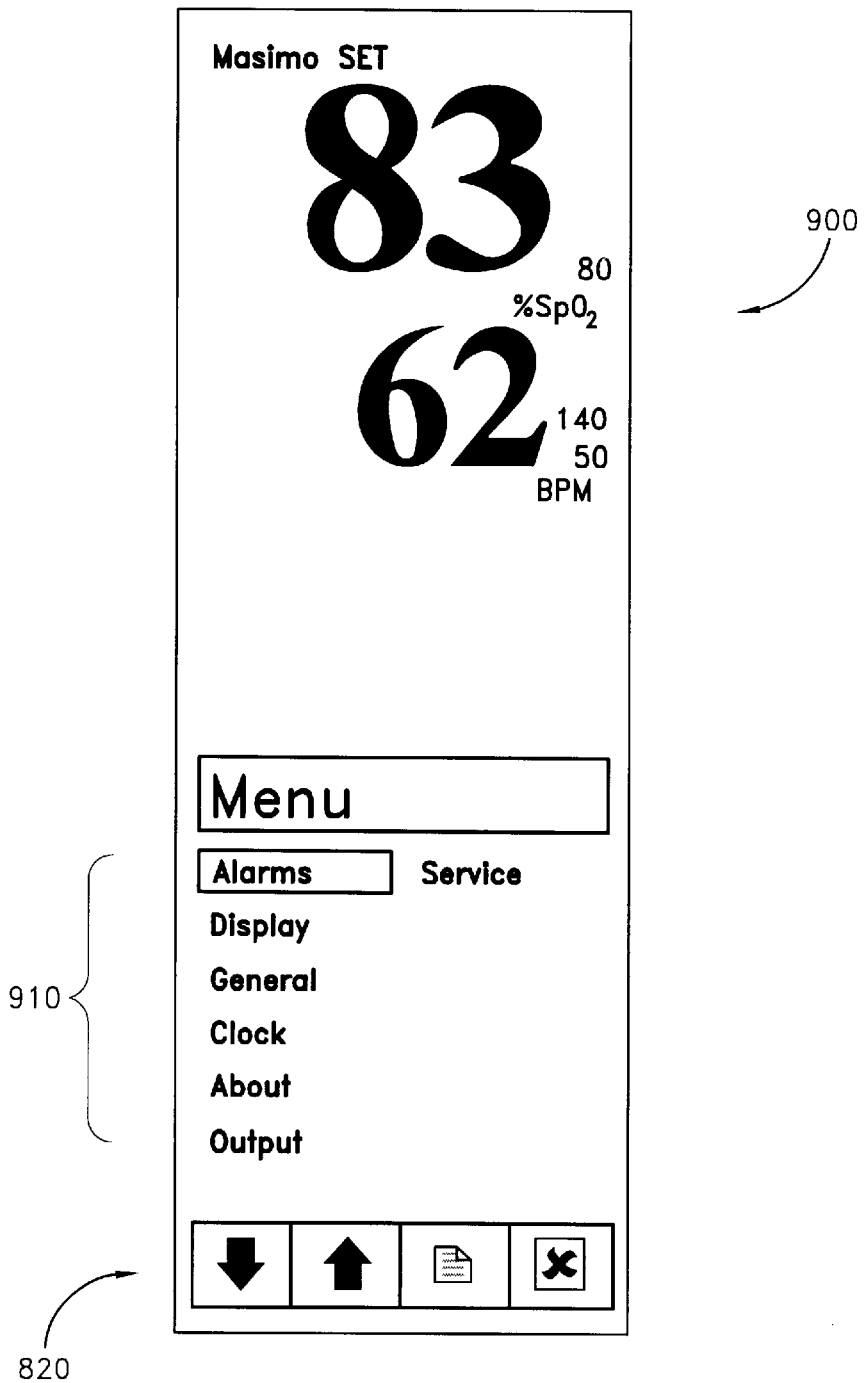
Figure 19:
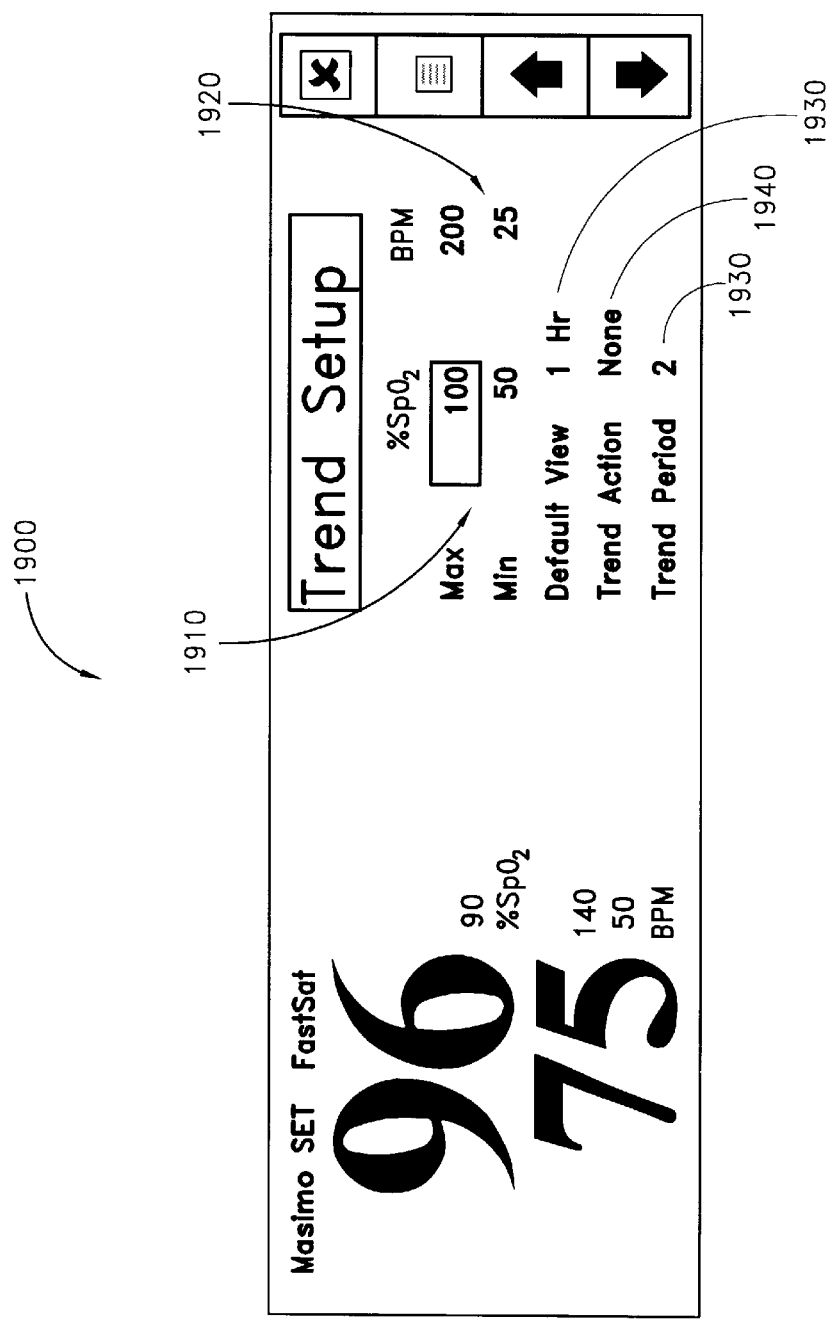
FIGS. 19–21 are illustrations of trend-related menus and screens accessible from the trend view.
Figure 20:
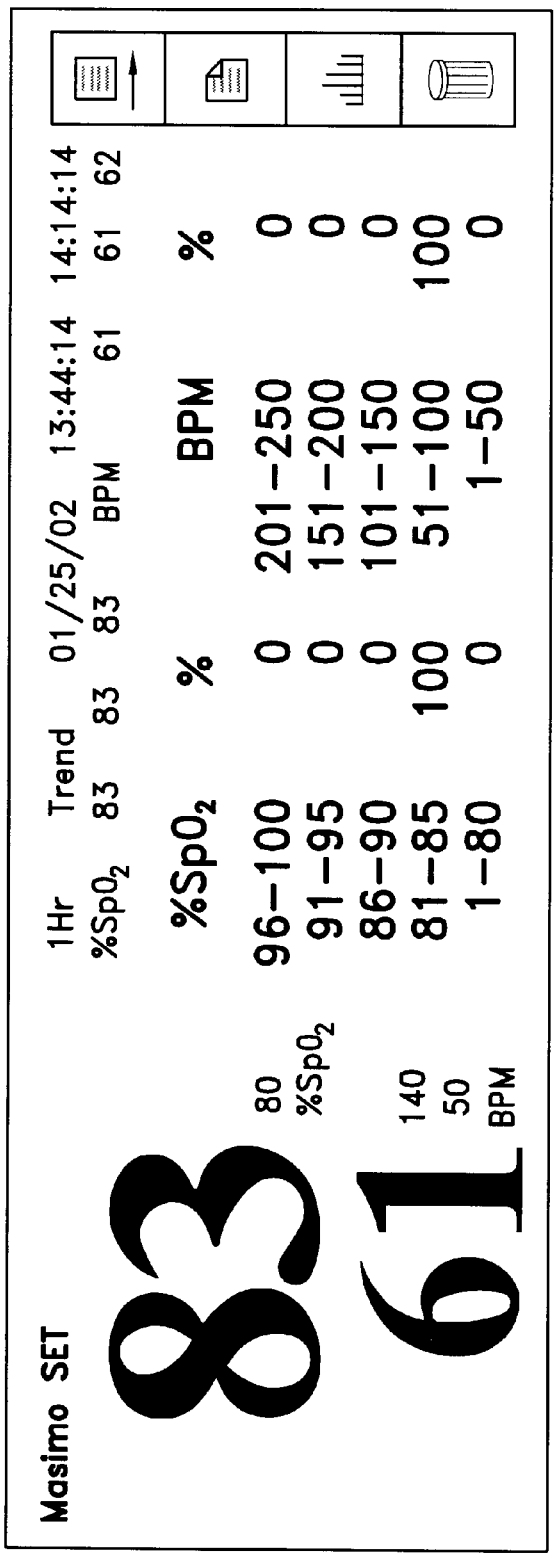
Figure 21:
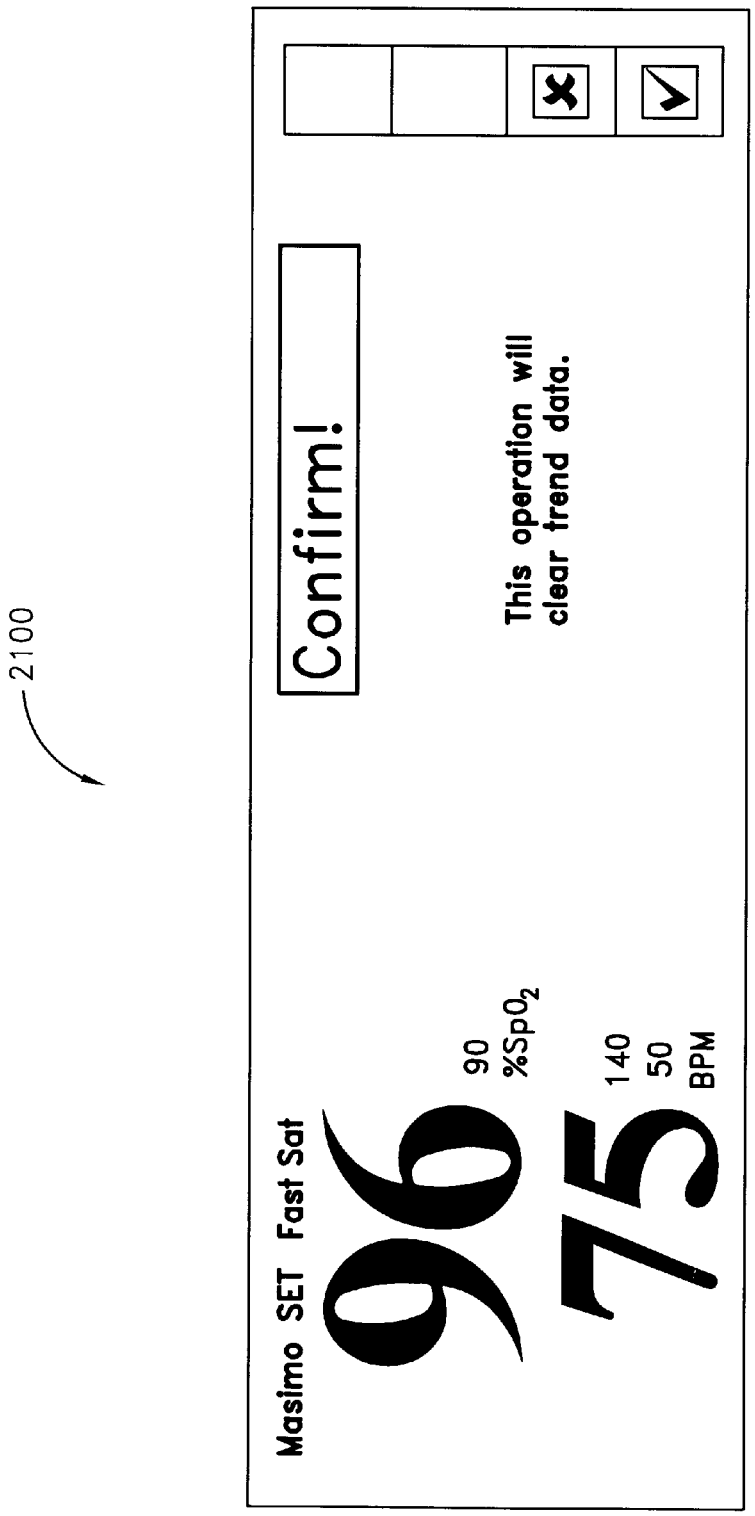

FIGS. 8A–B are hierarchical charts of soft key icons corresponding to the soft key buttons 260 (FIG. 2A). A soft key icon is selected by pressing and releasing the soft key button to the right of the icon (horizontal display) or underneath the icon (vertical display). Four icons are shown on the right side or bottom of the display. FIG. 8A illustrates a first set of soft key icons 801, including the first page of display view icons 810, menu icons 820, category icons 830 and parameter icons 840. FIG. 8B illustrates a second set of soft key icons 802, including the second page of display view icons 860 and trend-related icons 870–890. The display view icons 810 (FIG. 8A), 860 (FIG. 8B) are those icons initially shown on the three views 400 (FIG. 4), 500 (FIGS. 5A–B), 600 (FIG. 6), described above. The menu icons 820 (FIG. 8A) are those icons shown on the main menu 900 (FIGS. 9A–B). The category 830 and parameter 840 icons are those shown on the submenus 1100–1700 (FIGS. 11–17). The trend-related icons 870–890 (FIG. 8B) are those icons shown on the trend view 1000 (FIG. 10) and on the trend-related menus and screens 1900–2100 (FIGS. 19–21).

As shown in FIG. 8A, the first page of display view icons 810 include next page 812, menu access 814, increase loudness 816 and decrease loudness 818. Next page 812 is selected to access the second page of display view icons 860 (FIG. 8B). Menu access 814 is selected to enter the main menu 900 (FIGS. 9A–B). Increase loudness 816 is selected to increase the volume of the pulse beep. In one embodiment, there are seven levels of volume available. Decrease loudness 818 is selected to decrease the volume of the pulse beep. The lowest volume level will silence the pulse beep and the decrease loudness 818 icon will appear with a slash through it.

Figure 10:
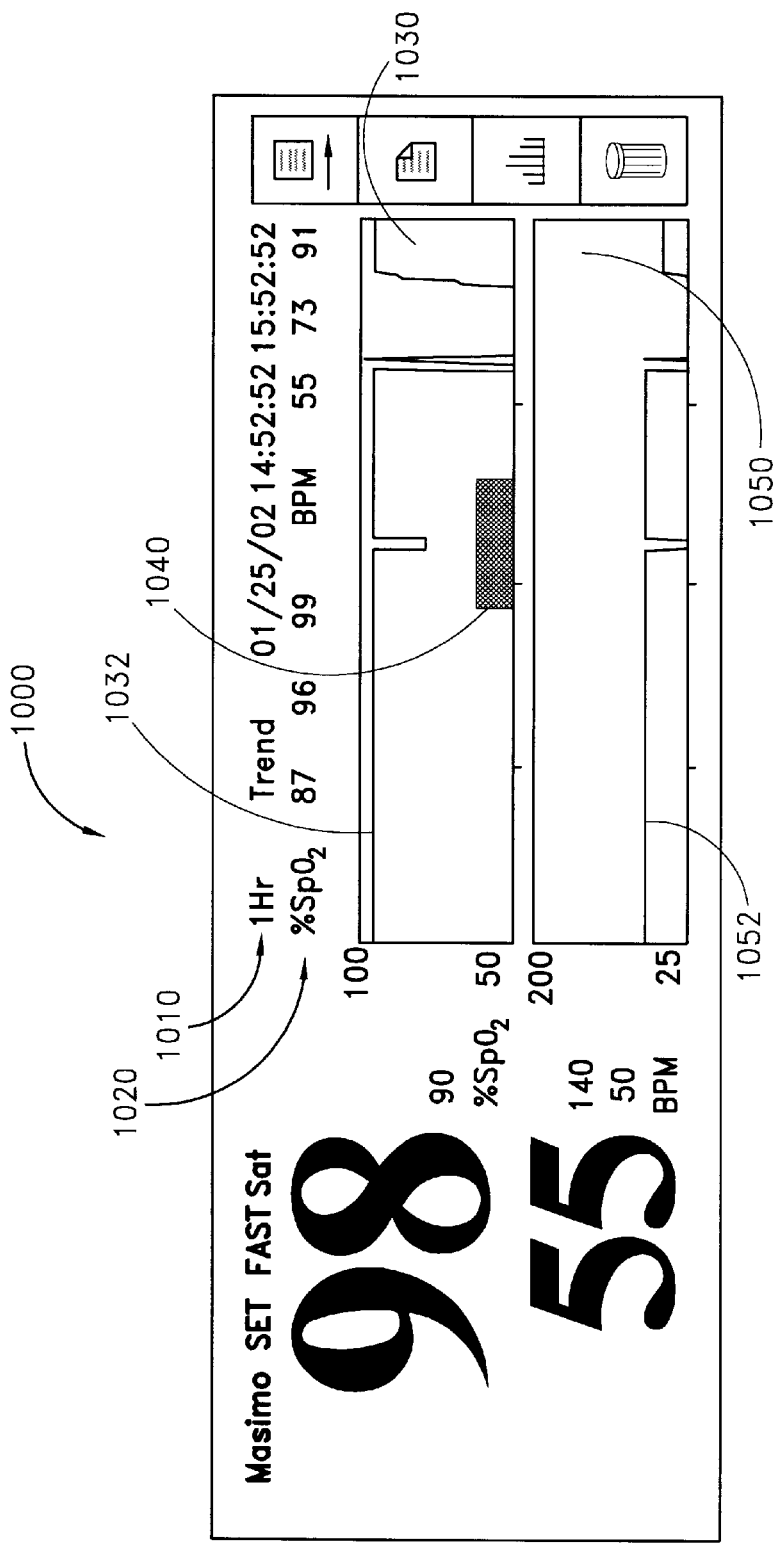
FIG. 10 is an illustration of a trend view.

As shown in FIG. 8B, the second page of display view icons 860 include next page 862, trend display 864, sensitivity 866 and rotate display 868. Next page 862 is selected to return to the first page of display view icons 810 (FIG. 8A). Trend display 864 is selected to show the trend view 1000 (FIG. 10). Sensitivity 866 is selected to toggle between normal and maximum sensitivity modes. Normal sensitivity is used for normal patient monitoring purposes. Maximum sensitivity is used for improved sensitivity performance on patients with extremely low perfusion. With the maximum sensitivity setting, the SENSOR OFF detection performance may be compromised. In one embodiment, the instrument automatically retains a sensitivity setting after a power cycle, and in another embodiment, the instrument does not retain a sensitivity setting after a power cycle. Rotate display 868 is selected to reconfigure the display contents in a vertical or horizontal format. The display contents rotate clockwise in 90 degree increments, accordingly.

Main Menu

FIGS. 9A–B illustrate horizontal and vertical formats, respectively, of a main menu 900. When the main menu 900 is accessed, the plethysmograph and signal quality waveform displays are replaced with main menu categories 910. The display view soft key icons 810 (FIG. 8A), 860 (FIG. 8B) are also replaced by the main menu soft key icons 820 (FIG. 8A). When the main menu 900 is accessed the instrument remains functional and the saturation and pulse rate numbers will continue to be displayed.

As shown in FIG. 8A, the main menu 900 (FIGS. 9A–B) uses the four main menu icons 820, including exit 822, select category 824, previous 826 and next 828. Exit 822 is selected to exit the main menu 900 (FIGS. 9A–B) and return to the original display view. Select category 824 is selected to choose a highlighted menu category 910 (FIGS. 9A–B) and display the corresponding submenu 1100–1700 (FIGS. 11–17). Previous 826 is selected to scroll through the menu categories 910 (FIGS. 9A–B), highlighting categories without selecting them. Next 828 is selected to scroll through the menu categories 910 (FIGS. 9A–B), in a direction opposite from previous 826, also highlighting categories without selecting them. Once a menu category 910 (FIGS. 9A–B) is highlighted, the chosen submenu 1100–1700 (FIGS. 11–17) is displayed with a select category 824 selection.

Also shown in FIG. 8A, a submenu 1100–1700 (FIGS. 11–17) is displayed with a set of category icons 830, including exit 832, edit parameter 834, previous 836 and next 838. Exit 832 is selected to exit the category submenu 1100–1700 (FIGS. 11–17) and return to the main menu 900 (FIGS. 9A–B). Edit parameter 834 is selected to choose a highlighted parameter in a submenu for editing. Previous 836 and next 838 function in a similar manner as described above to highlight parameters without selecting them. Once a parameter is highlighted, the parameter is edited by selecting edit parameter 834.

Further shown in FIG. 8A, once a parameter has been selected for editing, a set of parameter icons 840 are displayed, including exit 842, accept 844, previous 846 and next 848. Exit 842 is selected to exit a parameter without making any new selections permanent. Accept 844 is selected to save any changes. Previous 846 is selected to increase or toggle a parameter settings. Next 848 is selected to decrease or toggle a parameter settings. Submenus and associated parameters are described in more detail with respect to FIGS. 11–17, below.

Trend View

FIG. 10 illustrates a trend view 1000 having a first line of information 1010, a second line of information 1020, an oxygen saturation trend graph 1030, a low signal quality indicator 1040, and a pulse rate trend graph 1050. The first line 1010 on the trend view 1000 shows the time scale of the trend graph, followed by the starting date, starting time and end time of the data set that is displayed on the screen. The second line 1020 of the trend view 1000 shows the minimum, average, and maximum $SpO_2$ and pulse rate measurements contained in the displayed data set (excluding zero measurements). The oxygen saturation trend graph 1030 shows the $SpO_2$ measurements displayed versus time. The pulse rate trend graph 1050 shows the pulse rate measurements displayed versus time. A dark line 1032, 1034 on the trend graphs 1030, 1050 indicates averaged data, while grayed-out data points show minimum and maximum values. The low signal quality indicator 1040 appears as a grayed-out box, line or other designation located on the bottom axis or other portion of the oxygen saturation trend graph 1030 and indicates a period of time for which the "LOW SIGNAL IQ" message was active. During this time, the signal quality was very low and the accuracy of the measurement may have been compromised. The vertical scale of the oxygen saturation 1030 and pulse rate 1050 graphs can be set in the trend setup screen 1900 (FIG. 19).

Once the trend display icon 864 (FIG. 8B) is selected, the trend data is shown on the trend view 1000. The instrument stores one data set of oxygen saturation, pulse rate and system messages in a dedicated memory area. Depending on the trend period, a setting for how often the data is stored in the trend memory, the instrument can store between 72 hours and 30 days worth of trend data. The instrument also employs data compression. The actual amount of trend data that is stored is dependent on the type of data that is collected. The instrument only stores data in the trend memory while the instrument is turned on, and the trend data remains in memory until the memory fills up or is cleared by the user. Changing the date and time of the system clock or changing the trend period will also clear the data in the trend memory. The trend capacity for a trend period setting of 2 seconds is a minimum of 72 hours (3 days). For a trend period setting of 10 seconds, the trend memory capacity is typically 720 hours (30 days).

By default, the trend view 1000 automatically refreshes at a rate of once every 10 seconds, to show the latest measured $SpO_2$ and pulse rate data. This feature is only available while the trend view is 2 hours or less and the latest measured data is shown. If the user scrolls through the data set to display previously recorded trend data or if the trend scale is greater than 2 hours, the trend view will time out after 1 minute of inactivity (i.e. the user does not press any of the soft key buttons) and the previous display view will be shown.

As shown in FIG. 8B, in the trend view there are a total of 12 soft key icon selections 870–890 on 3 pages. The first page has next menu 872, exit 874, scroll left 876 and scroll right 878 icons. Next menu 872 is selected to access the next page of menu selections. Exit 874 is selected to return to the previous display view. Scroll left 876 is selected to scroll through the data set in the backward time direction. Scroll right 878 is selected to scroll through the data set in the forward time direction. The display scrolls by ½ the selected time scale. For example, if a 2 hr display view is selected, then selecting scroll left 876 or scroll right 878 will scroll the displayed data by 1 hr to the left or right, respectively.

Also shown in FIG. 8B, the second page has next menu 882, zoom 884, zoom from left 886, and zoom from right 888 icons. Next menu 882 is selected to access the next page of icons. Zoom 884 is selected to change the time scale of the trend view. The available time scales are 24 hrs, 12 hrs, 8 hrs, 4 hrs, 2 hrs, 1 hr, 30 minutes, 10 minutes, 1 minute and 20 seconds. Zoom 884 uses the last recorded data point as the zoom reference point. In other words, the last recorded data point is always shown as the right-most data point on the display. Zoom from left 886 is selected to zoom into the data set while keeping the data point that is shown on the right side of the trend graph as the zoom reference point. Zoom from right 888 is selected to zoom into the data set while keeping the data point that is shown on the left side of the trend graph as the zoom reference point.

Further shown in FIG. 8B, the third page has next menu 882, trend setup 884, histogram 896 and clear trend data 898 icons. Next menu 882 is selected to return to the first page of icons. Trend setup 884 is selected to enter the trend setup screen 1900 (FIG. 19). Histogram 896 is selected to display the selected data set (the data set shown in the trend view) in histogram format 2000 (FIG. 20). Clear trend data 898 is selected to clear the data stored in the trend memory, which is verified via a confirmation screen 2100 (FIG. 21).

Figure 11A:
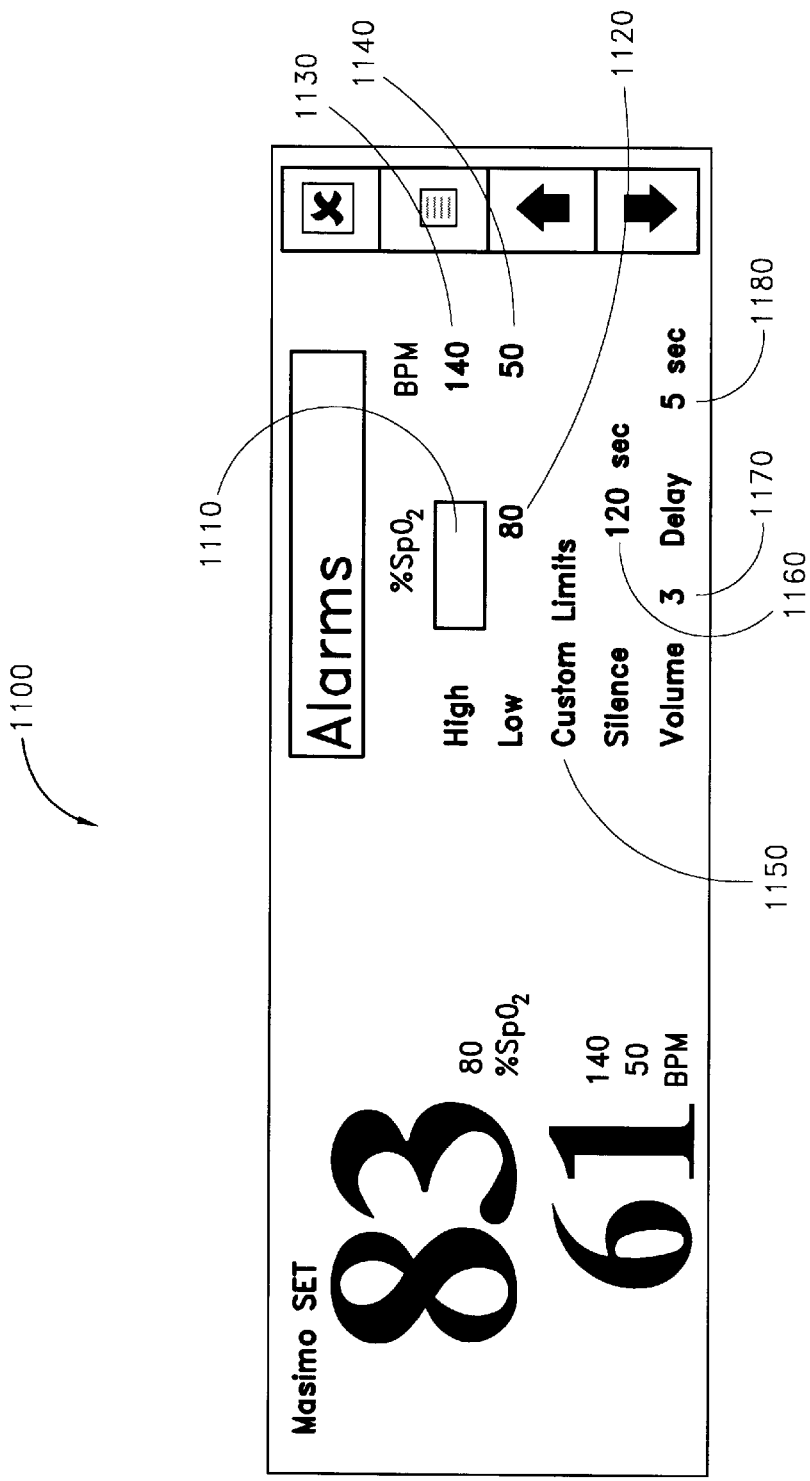
FIGS. 11A–B illustrate horizontal and vertical formats, respectively, of an alarm menu.
Figure 11B:
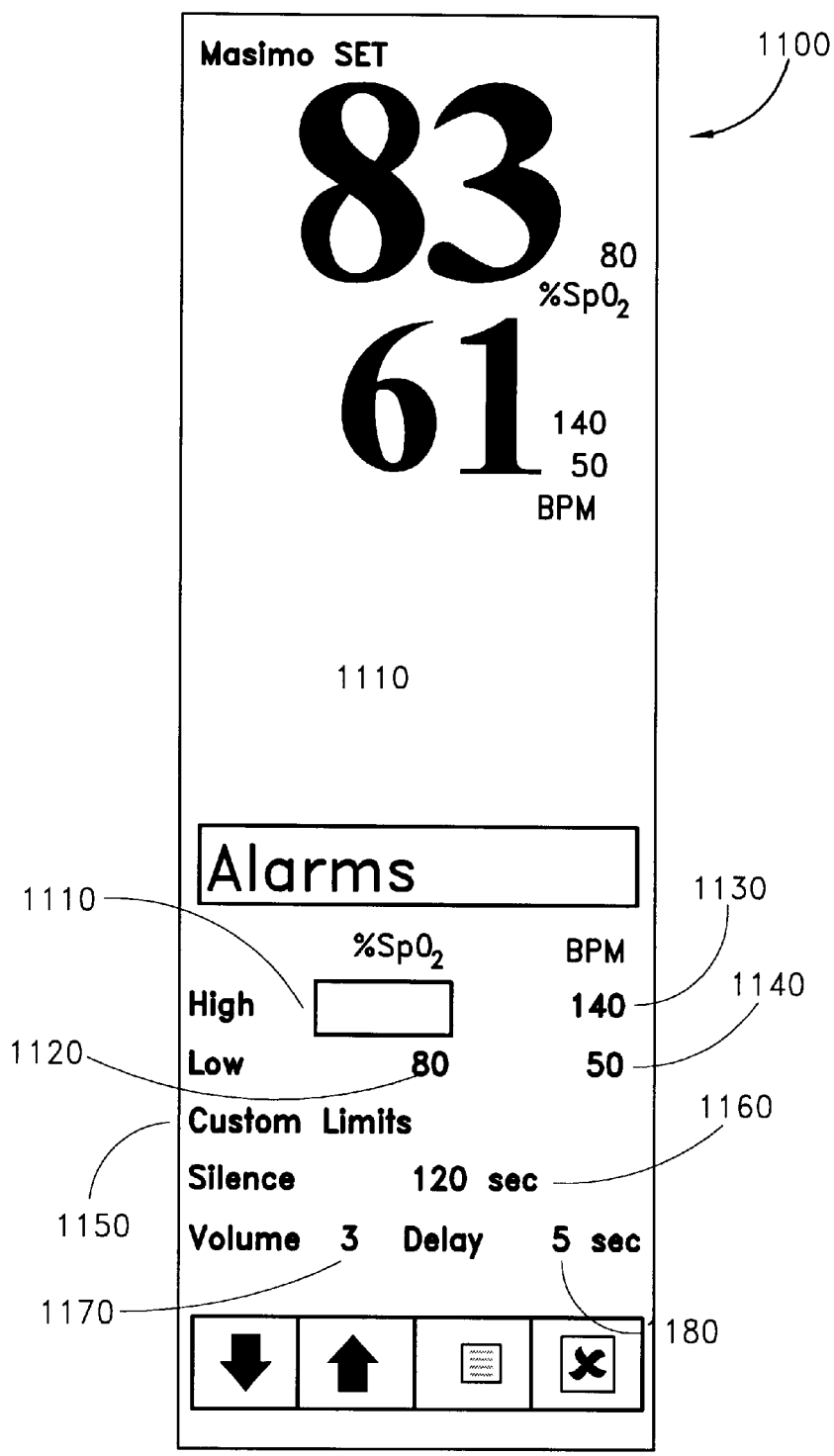

FIGS. 11A–B illustrate an alarms menu 1100 in horizontal and vertical formats, respectively, having a high $SpO_2$ alarm limit 1110, a low $SpO_2$ alarm limit 1120, a high pulse rate alarm limit 1130, and a low pulse rate alarm limit 1140. Alarm limit settings are typically checked each time the pulse oximeter is used to ensure that they are appropriate for the patient being monitored. An audible alarm and a flashing alarm status indicator 432 (FIG. 4) will occur when an alarm limit is met or exceeded.

The $SpO_2$ high alarm limit 1110 can be set anywhere between 2% and 100%, with a 1% step size. In the "—" (off) setting, the alarm can be turned off completely. The $SpO_2$ low alarm limit 1120 can be set anywhere between 1% and 100%, with a 1% step size. The pulse rate high alarm limit 1130 can be set anywhere between 30 BPM and 240 BPM, with a 5 BPM step size. The pulse rate low alarm limit 1140 can be set anywhere between 25 BPM and 235 BPM, with a 5 BPM step size. The low alarm limits 1120, 1140 always have to be set below the corresponding high alarm limits 1110, 1130. When a high alarm limit 1110, 1130 is set below the corresponding low alarm limit 1120, 1140, the low alarm limit 1120, 1140 will automatically adjust to the next setting below the newly entered high alarm limit 1110, 1130.

As shown in FIGS. 11A–B, the alarms menu 1100 also has alarm limit type 1150, silence 1160, volume 1170 and delay 1180 settings. The instrument stores three alarm limit types 1150 including adult, neo and custom limits. Adult and neo limits are preset and cannot be changed by the user. Table 1 outlines the default values of the preset and custom alarm limit types 1150.

TABLE 1

| TYPES | $SpO_2$ HIGH | $SpO_2$ LOW | PR HIGH | PR LOW |
|---|---|---|---|---|
| Adult | Off | 90% | 140 BPM | 50 BPM |
| Neo | 100% | 90% | 180 BPM | 100 BPM |
| Custom | Off | 90% | 140 BPM | 50 BPM |

The custom limits are set to the values listed in the table at the factory. Once the values are changed, the new values are retained after a power cycle.

The alarm menu 1100 allows the user to set an alarm silence duration 1160. An alarm is silenced by pressing the alarm silence button 230 (FIG. 2A) on the front panel. The alarm silence duration 1160 can be virtually any amount of time. However, in a preferred embodiment, the duration 1160 is set as 30, 60, 90 and 120 seconds. As an indicator that the alarm system is silenced, the alarm status indicator 436 (FIG. 4) is shown as a bell with a slash through it. A timer is shown next to the bell indicating the remaining alarm silence duration. The alarm silence duration 1160 is reset to 120 seconds upon a power cycle, except for when the instrument is set to operate in the home mode. In an all mute mode, all patient alarm conditions are silenced. Only system alarms will be indicated by an audible alarm. As an indicator that the system is set to all mute, the alarm status indicator 436 (FIG. 4) is shown as a flashing bell with a slash through it. In an all mute with audible reminder mode, all patient alarm conditions are silenced. Only system alarms will be indicated by an audible alarm. As a reminder, a single audible alarm will occur every three minutes.

Also shown in FIGS. 11A–B, the alarm menu 1100 allows the user to set the alarm volume 1170. According to one embodiment, four levels are available, with level 1 being the softest and level 4 being the loudest. The instrument retains the alarm volume 1170 setting upon a power cycle. For home use, the alarm level to typically set to level 4. If an alarm condition occurs while the alarm silence period is set to all mute, the only alarm indications will be visual displays and symbols related to the alarm condition. No alarm tone will sound.

Figure 12:
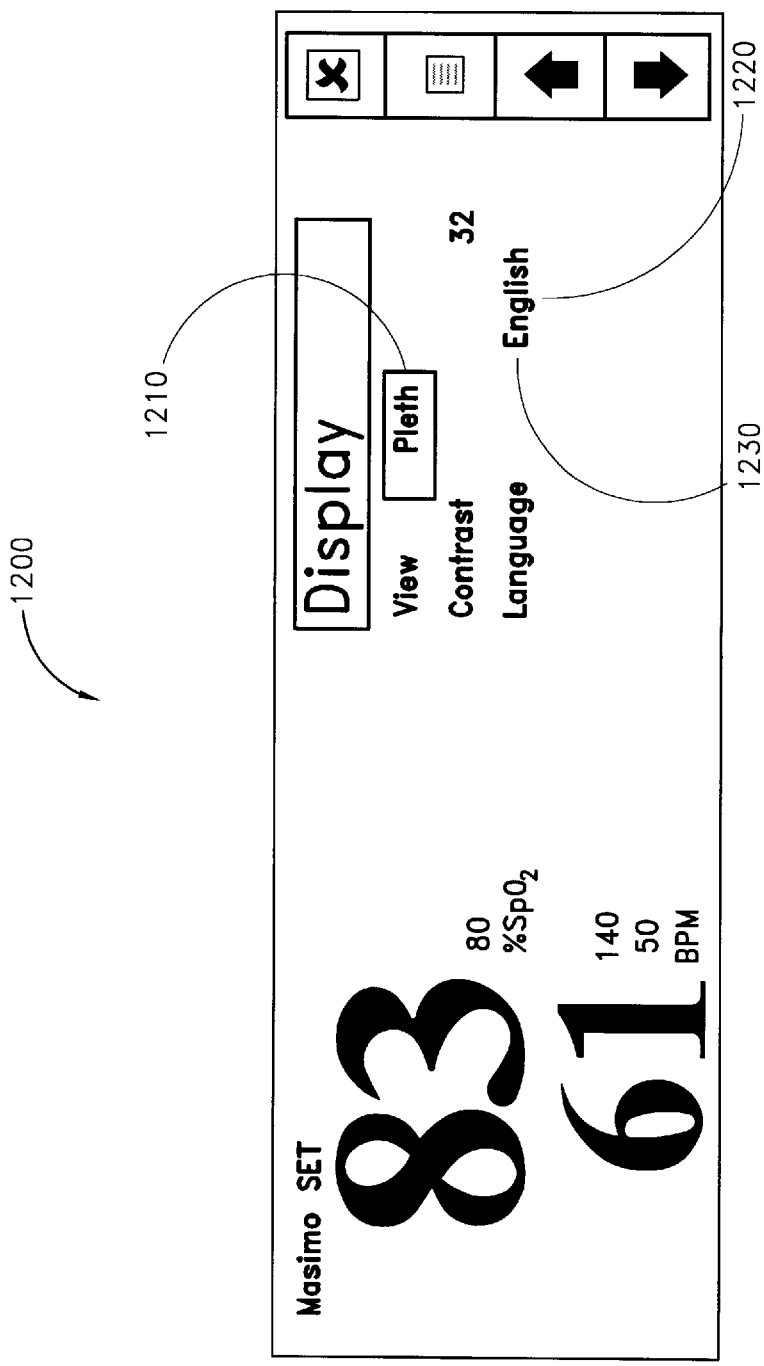

FIG. 12 illustrates the display menu 1200 having display view 1210, contrast 1220 and language 1230 items. The display view item 1210 allows selection of one of the three display views including pleth 400 (FIG. 4), pleth and signal quality 500 (FIGS. 5A–B) and numeric 600 (FIG. 6), described above. The contrast item 1220 allows the user to set the display contrast. According to one embodiment, contrast ranges from 1 to 64. The contrast can also be set by pressing and holding the backlight/contrast key 240 (FIG. 2A) on the front panel. The language item 1230 allows the user to select the display language.

Figure 13:
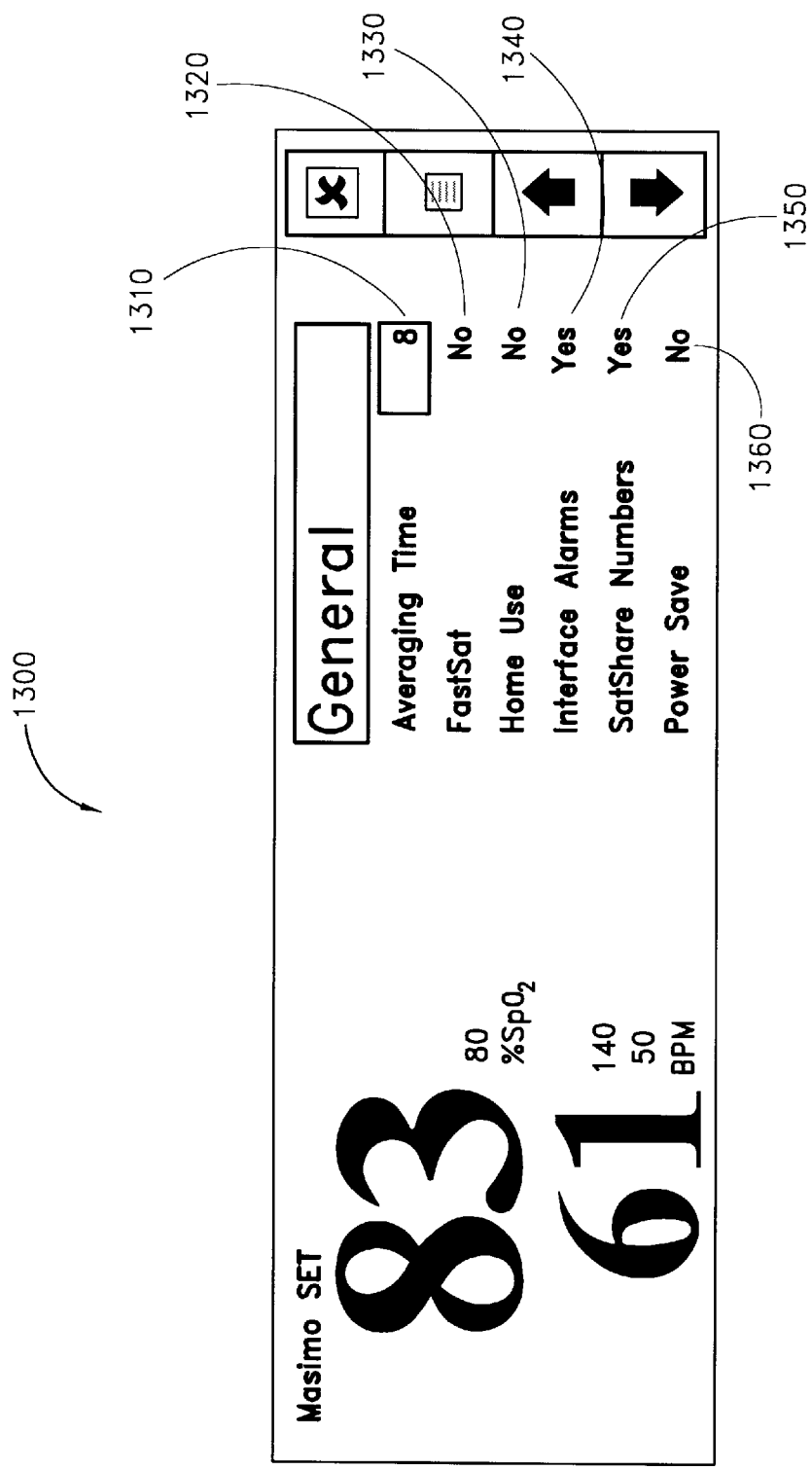

FIG. 13 illustrates a general menu 1300 having averaging time 1310, FastSat 1320, home use 1330, interface alarms 1340, SatShare numbers 1350 and power save 1360 items. Averaging time 1310 is the signal averaging time of the instrument, which can be set to include 2, 4, 8, 10, 12, 14 and 16 seconds. FastSat 1320, when set to "yes," activates a fast signal processing algorithm, such as described in U.S. patent application Ser. No. 09/586,845 referenced above. In the 2 and 4 seconds averaging mode, the fast signal processing algorithm is automatically enabled. With fast signal processing, the averaging time is dependent on the input signal. For the 2 and 4 second settings, the averaging times may range from 2–4 and 4–6 seconds, respectively.

As shown in FIG. 13, home use 1330, when set to "yes," places the instrument in the home mode, where it remains until the "no" setting is selected. A password is required to activate or deactive this mode. Home use operation is described further with respect to FIG. 18, below. Interface alarms 1340 allows audible alarms to be enabled or disabled. SatShare numbers 1350 is set to "yes" to display saturation and pulse rate measurements during upgrade operation, as described with respect to FIG. 1C, above.

Also shown in FIG. 13, power save 1360 can be set to "yes" or "no," to adjust battery-operating time of the instrument while powered by the handheld battery or optional docking station battery. Selecting "yes" disables docking station functions such as the interface cable, serial and analog outputs. Selecting "no" activates these docking station functions while operating on battery power. While operating in the power save mode, a power cycle of the instrument may be required to activate the docking station again after it has been disabled.

FIG. 14 illustrates a clock menu 1400 having time 1410, time format 1420, date 1430 and date format 1440 items. The time item 1410 sets the hour and minutes. The time format item 1420 sets the time display in 12 hour (default) and 24 hour format. The date item 1430 sets the day, month and year. The date format item 1440 sets the date display in mm/dd/yyyy (default) and dd/mm/yyyy format.

Figure 15:
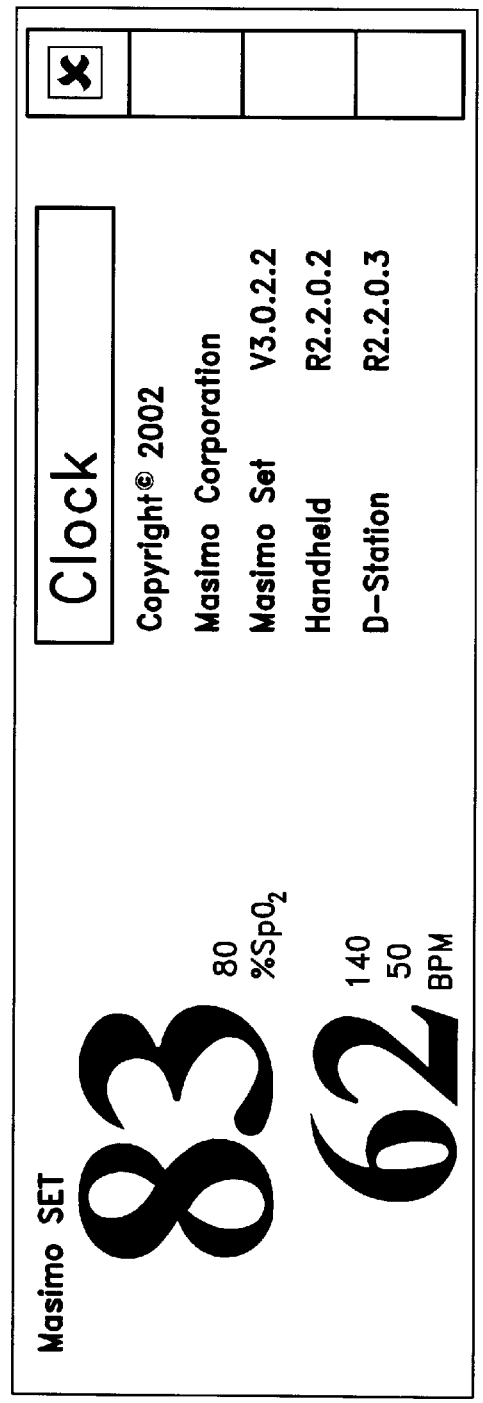

FIG. 15 illustrates the about screen 1500. The about screen 1500 simply displays the copyright and software versions of the handheld 101 (FIG. 1A) and the docking station 103 (FIG. 1B).

Figure 16:
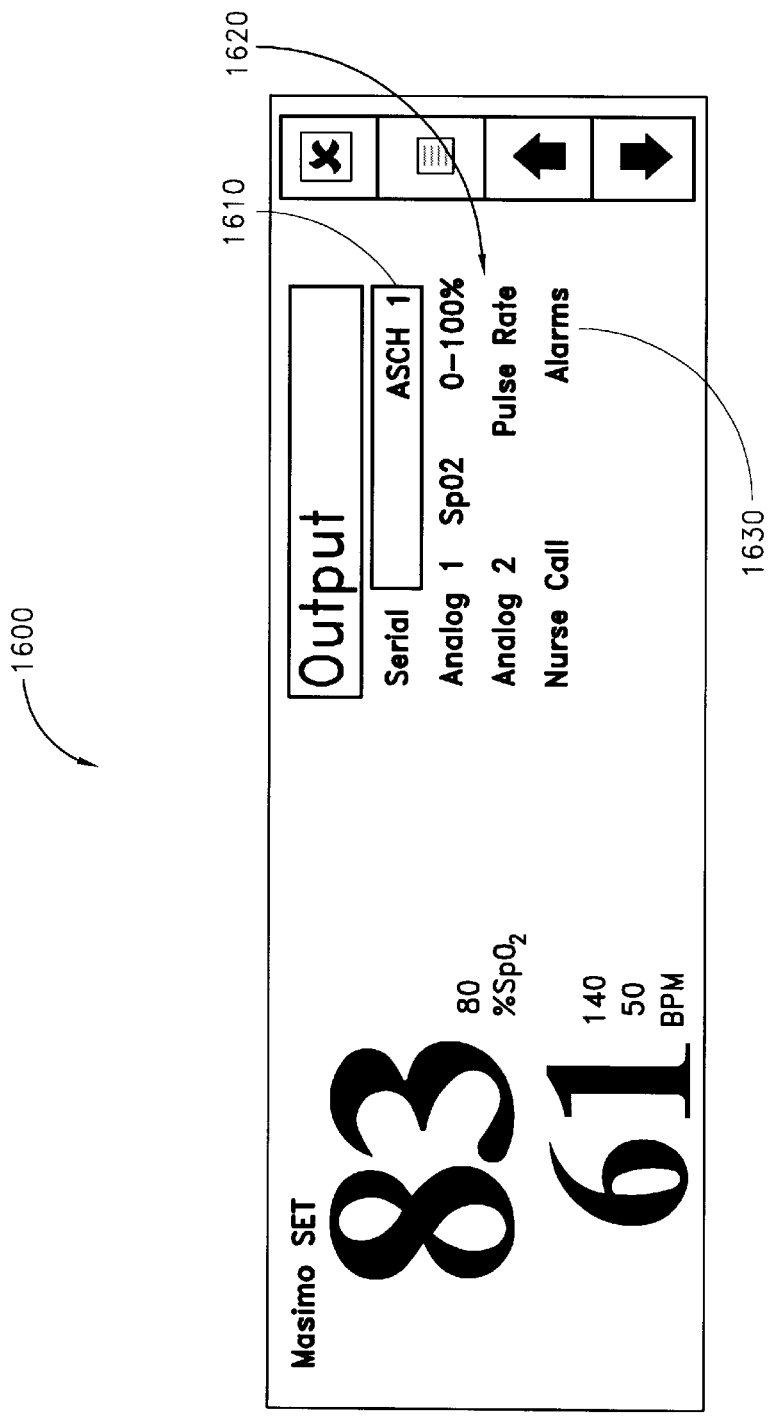

FIG. 16 illustrates the output menu 1600 having serial 1610, analog 1620 and nurse call 1630 output modes. The output menu selections are available when the handheld 101 (FIG. 1A) is interfaced to the docking station 103 (FIG. 1B). The serial item 1610 allows a user to specify various serial output modes, which, according to one embodiment, are RS-232 based. In ASCII 1 mode, for example, ASCII text data is sent to the serial interface at one-second intervals. The ASCII text includes date and time stamp, $SpO_2$ pulse rate, PI, and alarm and exception values. All text is single line followed by a line feed character and a carriage return. In ASCII 2 mode, ASCII text data is sent to the serial interface following a query from the connecting computer.

The analog items 1620 specify the docking station analog outputs. In 0%–100% mode, the saturation measurement is scaled with 0% being equal to 0 volts and 100% equal to 1 volt. In 50%–100% mode, the saturation measurement is scaled with 50% being equal to 0 volts and 100% equal to 1 volt. In the 0V mode, a 0 volts calibration signal is mapped onto the analog outputs. This signal is used for calibration of recording devices, where 0 volts represent a saturation of 0% and a pulse rate of 0 bpm. In the 1V mode, a 1 volt calibration signal is mapped onto the analog outputs. This signal is also used for calibration of recording devices, where 1 volt represents a saturation of 100% and a pulse rate of 250 bpm. In pleth mode, the pulse waveform is scaled with 1 volt being equal to 100% full scale. In signal IQ mode, 1 volt is equal to maximum signal quality. The nurse call item 1630 can specify alarms and low signal quality as generating a nurse call.

Figure 17:
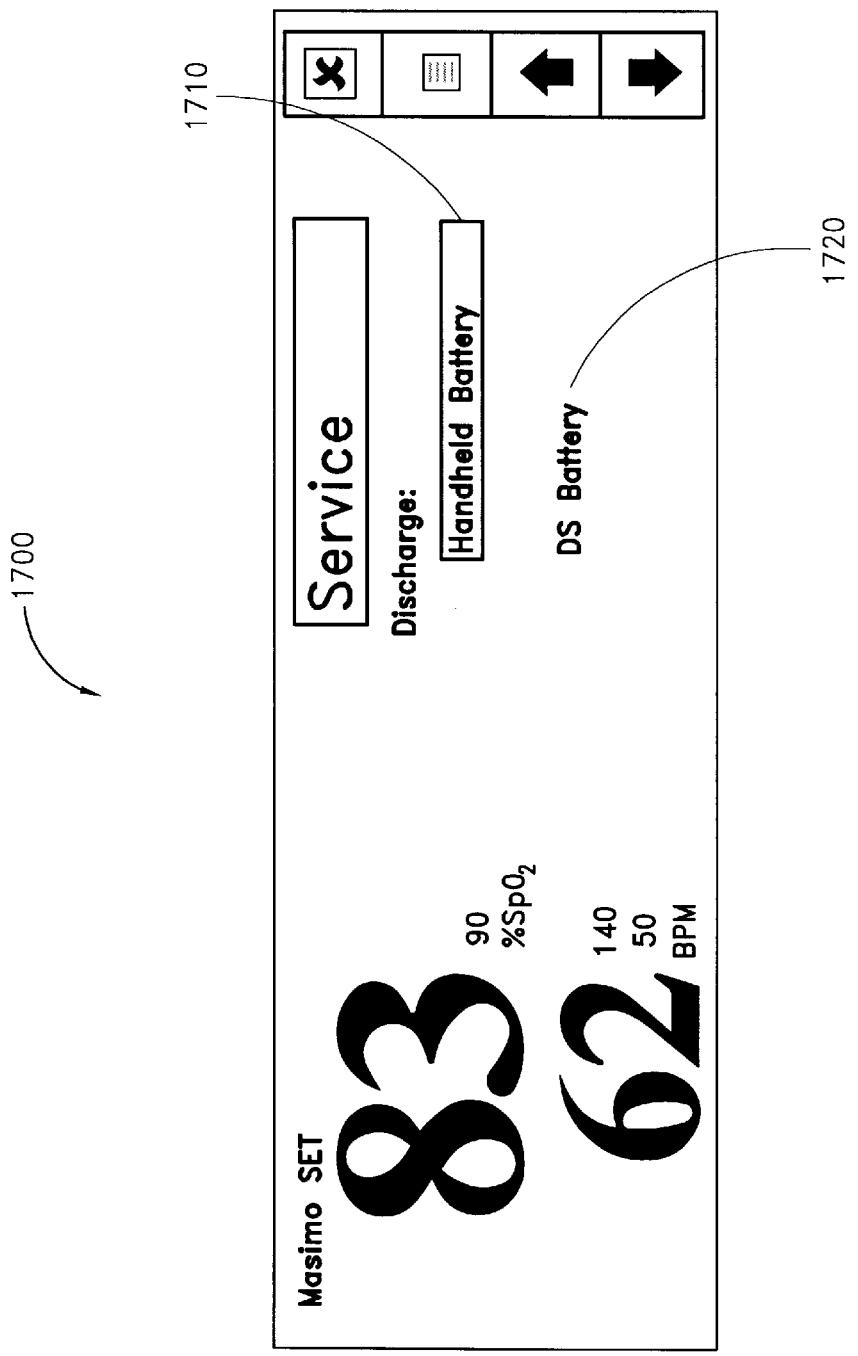

FIG. 17 illustrates a service menu 1700 having handheld battery discharge 1710 and docking station (DS) battery discharge 1720 items. The service menu 1700 selections are only available when the handheld 101 (FIG. 1A) is interfaced to the docking station 103 (FIG. 1B). Each of these items 1710, 1720, when selected, causes the instrument to perform a deep discharge the respective handheld or docking station battery. The discharge cycle will take approximately 16 hours to complete for the handheld battery and approximately 30 hours to complete for the docking station battery. A message will appear in the service screen when the discharge cycle is complete. The batteries will be fully charged after completion of the cycle.

Figure 18:
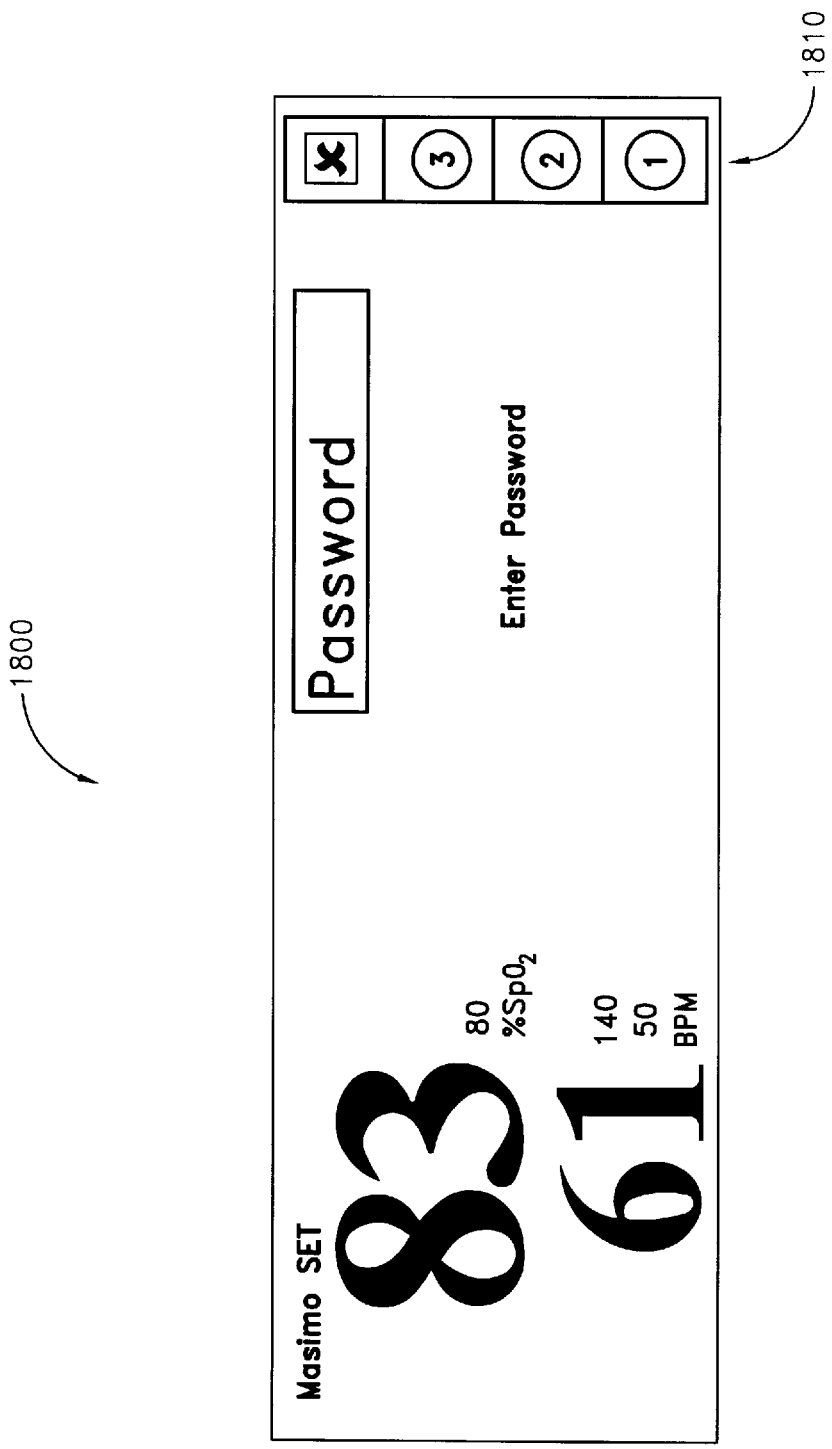

FIG. 18 illustrates a password entry display 1800. A password is entered using the password soft key icons 1810 and pressing in a particular sequence the corresponding soft key buttons 260 (FIG. 2A) to the right or bottom of the display. In a home mode, a password is required to access the menu system and the soft key buttons and icons. When the instrument is set to operate in the home mode, the default values that the instrument reverts to after a power cycle are set according to a predetermined setting with the exception of the alarm silence setting, which is set to the pre-power down setting. The instrument can be placed into the home mode to protect unqualified users from changing the alarm settings and operation. Entering a password does not automatically reset the instrument to a normal operating mode. To return to a normal operating mode, the home use parameter 1330 (FIG. 13) is set to "No" in the general menu 1300 (FIG. 13).

FIG. 19 illustrates a trend setup menu 1900 having %SpO$_2$ max and min 1910, BPM max and min 1920, default view 1930, trend action 1940 and trend period 1950 items. The trend setup menu 1900 allows the user to set the default trend settings and to clear the trend data or download the trend data to the serial port. The default settings are used to scale the trend graphs when the trend data icon 864 (FIG. 8B) is selected. %SpO$_2$ max and min 1910 set the high and low scale, respectively, of the SpO$_2$ trend graph 1030 (FIG. 10). BPM max and min 1920 set the high scale, respectively, of the pulse rate trend graph 1050 (FIG. 10). Default view 1930 selects the default time scale of the trend view 1000 (FIG. 10). This setting only selects the time scale of the trend view 1000 (FIG. 10) when the trend data is initially displayed, (i.e. when the trend data is initially accessed). According to one embodiment, the selections include 24 hrs, 12 hrs, 8 hrs, 4 hrs, 2 hrs, 1 hr, 30 minutes, 10 minutes, 1 minute and 20 seconds.

As shown in FIG. 19, trend action 1940 has serial dump, analog dump and print options. The serial dump option sends all the data that is stored in trend memory to the serial port and is used to communicate the stored data set to trend graphing software applications. The analog dump option sends all the data that is stored in the trend memory to the analog output and is used to print the trend information on an analog chart recorder. The print option prints the trend data that is shown in the trend view 1000 (FIG. 10). The trend data is first printed in histogram format, followed by a table of data that shows the time and date stamp of a trend record and the SpO$_2$ and pulse rate measurement. Each trend record is printed on a single line, followed by a carriage return and line feed character.

Also shown in FIG. 19, trend period 1950 determines how often a set of SpO$_2$ and pulse rate data points is stored in trend memory. A setting of 2, for example, sets the instrument to store one set of SpO$_2$ and pulse rate measurements every 2 seconds, resulting in a minimum trend capacity of 72 hours. A setting of 10, for example, sets the instrument to store one set of data points every 10 seconds, resulting in a typical trend storage capacity of 30 days. Because of data compression, the actual trend capacity is dependent on the type of data that is collected.

A pulse oximetry user interface has been disclosed in detail in connection with various embodiments. These embodiments are disclosed by way of examples only and are not to limit the scope of the claims that follow. One of ordinary skill in the art will appreciate from the disclosure herein any variations and modifications.

Additionally, all publications, patents, and patent applications mentioned in this specification are herein incorporated by reference to the same extent as if each individual publication, patent, or patent application was specifically and individually indicated to be incorporated by reference.

What is claimed is:

1. A pulse oximetry user interface comprising:
   a display;
   a plurality of views each configured to occupy said display, each of said views adapted to present data responsive to a physiological signal;
   a plurality of icons configured to occupy a portion of said views and adapted to designate the content of said views;
   a plurality of keys proximate to said display and corresponding to said icons so as to select said icons;
   a scale associated with said pulse waveform;
   a signal strength measure corresponding to said physiological signal; and
   a relationship between said signal strength and said scale so that said pulse waveform conveys information regarding said signal strengths,
   wherein one of said views presents a pulse waveform, another of said views presents a trend graph, and at least one of said icons can be selected so as to switch said display between said one view and another view.

2. The pulse oximetry user interface according to claim 1 wherein said relationship is a piecewise-linear auto-scaling function.

3. The pulse oximetry user interface according to claim 2 wherein
   said pulse waveform is about 90% full scale for signal strengths in the range of about 10% to 20% DC;
   said pulse waveform is in the range of about 60% to 90% full scale for signal strengths in the range of about 2% to 10% DC;
   said pulse waveform is in the range of about 15% to 60% full scale for signal strengths in the range of about 0.5% to 2% DC; and
   said pulse waveform is about 15% full scale for signal strengths in the range of about 0.02% to 0.5% DC.

4. A pulse oximetry user interface method comprising the steps of:
   deriving a pulse waveform responsive to a physiological signal;
   calculating a data trend responsive to said physiological signal;
   providing said pulse waveform in a first display view;
   presenting at least a portion of said data trend in a second display view;
   selecting a first icon accessible from said first display view to switch to said second display view;
   selecting a second icon accessible from said second display view to switch to said first display view;
   determining a signal strength for said physiological signal; and
   scaling said pulse waveform according to a piecewise linear relationship so as to be responsive to said signal strength.

5. A pulse oximetry user interface method comprising the steps of:
   deriving a pulse waveform responsive to a physiological signal;
   calculating a data trend responsive to said physiological signal;
   providing said pulse waveform in a first display view;
   presenting at least a portion of said data trend in a second display view;
   selecting a first icon accessible from said first display view to switch to said second display view;
   selecting a second icon accessible from said second display view to switch to said first display view;
   determining a first portion of said data trend corresponding to a first time period;

determining a second portion of said data trend corresponding to a second time period, where said first time period and said second time periods are about equal; and selecting said first portion or said second portion for said second display view based on a scroll icon provided in said second display view.

6. A pulse oximetry user interface method comprising the steps of:

deriving a pulse waveform responsive to a physiological signal;

calculating a data trend responsive to said physiological signal;

providing said pulse waveform in a first display view;

presenting at least a portion of said data trend in a second display view;

selecting a first icon accessible from said first display view to switch to said second display view;

selecting a second icon accessible from said second display view to switch to said first display view;

determining a first portion of said data trend corresponding to a first time period;

determining a second portion of said data trend corresponding to a second time period, where said first time period is an integral multiple larger than said second time periods; and selecting said first portion or said second portion for said second display view based on a zoom icon provided in said second display view.

7. A pulse oximetry user interface comprising:

a view means for presenting to a user data responsive to a physiological signal;

a main menu means for choosing display related categories;

a category menu means for choosing display related parameters, said parameters determining the characteristic of said view means;

an icon means for designating said view means, accessing said menu means and altering said parameters;

a soft key means for selecting said icon means a pulse waveform portion of said view means responsive to said physiological signal; and an auto-scaling means applied to said pulse waveform portion for indicating the signal strength of said physiological signal.

* * * * *

UNITED STATES PATENT AND TRADEMARK OFFICE
CERTIFICATE OF CORRECTION

PATENT NO. : 6,658,276 B2
DATED : December 2, 2003
INVENTOR(S) : Massi E. Kiani et al.

It is certified that error appears in the above-identified patent and that said Letters Patent is hereby corrected as shown below:

<u>Title page,</u>
Item [75], Inventors, change "Massi E. Kianl" to -- Massi E. Kiani --.

Signed and Sealed this

Twenty-seventh Day of December, 2005

JON W. DUDAS
*Director of the United States Patent and Trademark Office*